(12) United States Patent  
Callaghan et al.

(10) Patent No.: US 8,231,619 B2  
(45) Date of Patent: Jul. 31, 2012

(54) STERILIZATION DEVICE AND METHOD

(75) Inventors: David Callaghan, Mansfield, MA (US); Matthew LaPlaca, Cumberland, RI (US); Jeffrey Model, Cambridge, MA (US); Mark Putnam, Weymouth, MA (US); James Duronio, Westford, MA (US)

(73) Assignee: Cytyc Corporation, Marlborough, MA (US)

( * ) Notice: Subject to any disclaimer, the term of this patent is extended or adjusted under 35 U.S.C. 154(b) by 203 days.

(21) Appl. No.: 12/692,057

(22) Filed: Jan. 22, 2010

(65) Prior Publication Data

US 2011/0180073 A1    Jul. 28, 2011

(51) Int. Cl.
*A61B 18/12* (2006.01)

(52) U.S. Cl. ............... 606/41; 606/42; 606/52; 128/898

(58) Field of Classification Search .................. 128/898; 606/28, 41–50; 607/138
See application file for complete search history.

(56) References Cited

U.S. PATENT DOCUMENTS

| | | |
|---|---|---|
| 2,102,270 A | 12/1937 | Hyams |
| 3,680,542 A | 8/1972 | Cimber |
| 3,805,767 A | 4/1974 | Erb |
| 3,840,016 A | 10/1974 | Lindemann |
| 3,858,571 A | 1/1975 | Rudolph |
| 3,858,586 A | 1/1975 | Lessen |
| 3,918,431 A | 11/1975 | Sinnreich |
| 3,938,527 A | 2/1976 | Rioux et al. |
| 3,949,736 A | 4/1976 | Vrana et al. |
| 3,953,566 A | 4/1976 | Gore |
| RE29,345 E | 8/1977 | Erb |
| 4,052,754 A | 10/1977 | Homsy |
| 4,057,063 A | 11/1977 | Gieles et al. |
| 4,060,088 A | 11/1977 | Morrison, Jr. et al. |
| 4,185,618 A | 1/1980 | Corey |
| 4,245,643 A | 1/1981 | Benzing, III et al. |
| 4,258,721 A | 3/1981 | Parent et al. |
| 4,311,145 A | 1/1982 | Esty et al. |

(Continued)

FOREIGN PATENT DOCUMENTS

AU    B-59403/96    2/1997

(Continued)

OTHER PUBLICATIONS

Brumsted, Attempted Transcervical Occlusion of the Fallopian Tube with the ND: Yag Laser, 77 Obstetrics and Gynecology 327-28 (Feb. 1991).

(Continued)

*Primary Examiner* — Aaron Roane
(74) *Attorney, Agent, or Firm* — Robert P. Smith

(57) ABSTRACT

Sterilization devices and methods for deploying porous implants within the fallopian tubes are disclosed. The devices include a catheter component including an external electrode sheath containing at least two deployable implants and a positioning member. Sliding the external sheath proximally disposes the implants within the fallopian tubes, while sliding both the positioning member and external electrode sheath distally reloads a second implant into the external electrode sheath. The devices further includes a handle component, which houses a chassis, external electrode sheath carrier, reciprocating shaft, positioning member carrier and first and second engaging members. The reciprocating shaft may be operated by a motor to slide distally and proximally along a long axis. The reciprocating shaft, external electrode sheath and its carrier, upon selective actuation, move together proportionally to deploy and reload the implants to facilitate occlusion of the fallopian tubes and complete sterilization.

19 Claims, 13 Drawing Sheets

U.S. PATENT DOCUMENTS

| | | |
|---|---|---|
| 4,345,602 A | 8/1982 | Yoshimura et al. |
| 4,416,660 A | 11/1983 | Dafoe |
| 4,474,179 A | 10/1984 | Koch |
| 4,509,504 A | 4/1985 | Brundin |
| 4,512,342 A | 4/1985 | Zaneveld et al. |
| 4,523,590 A | 6/1985 | Roth et al. |
| 4,537,186 A | 8/1985 | Verschoof et al. |
| 4,606,336 A | 8/1986 | Zeluff |
| 4,641,634 A | 2/1987 | Storz |
| 4,700,701 A | 10/1987 | Montaldi |
| 4,779,611 A | 10/1988 | Grooters et al. |
| 4,781,175 A | 11/1988 | McGreevy et al. |
| 4,788,966 A | 12/1988 | Yoon |
| 4,793,326 A | 12/1988 | Shishido |
| 4,834,091 A | 5/1989 | Ott |
| 4,900,303 A | 2/1990 | Lemelson |
| 4,907,158 A | 3/1990 | Kettler et al. |
| 4,966,597 A | 10/1990 | Cosman |
| 4,994,069 A | 2/1991 | Ritchart et al. |
| 5,009,655 A | 4/1991 | Daignault, Jr. et al. |
| 5,095,917 A | 3/1992 | Vancaillie |
| 5,098,430 A | 3/1992 | Fleenor |
| 5,122,137 A | 6/1992 | Lennox |
| 5,147,353 A | 9/1992 | Everett |
| 5,152,784 A | 10/1992 | Tsilibary |
| 5,167,658 A | 12/1992 | Ensslin |
| 5,203,344 A | 4/1993 | Scheltinga et al. |
| 5,256,138 A | 10/1993 | Burek et al. |
| 5,303,719 A | 4/1994 | Wilk et al. |
| 5,304,194 A | 4/1994 | Chee et al. |
| 5,320,091 A | 6/1994 | Grossi et al. |
| 5,341,804 A | 8/1994 | Fogt et al. |
| 5,341,807 A | 8/1994 | Nardella |
| 5,366,476 A | 11/1994 | Noda |
| 5,383,922 A | 1/1995 | Zipes et al. |
| 5,391,010 A | 2/1995 | Gorbunov |
| 5,391,146 A | 2/1995 | That et al. |
| 5,395,342 A | 3/1995 | Yoon |
| 5,458,585 A | 10/1995 | Salmon et al. |
| 5,458,640 A | 10/1995 | Gerrone |
| 5,460,628 A | 10/1995 | Neuwirth et al. |
| 5,469,857 A | 11/1995 | Laurent et al. |
| 5,490,845 A | 2/1996 | Racz |
| 5,505,686 A | 4/1996 | Willis et al. |
| 5,531,741 A | 7/1996 | Barbacci |
| 5,536,267 A | 7/1996 | Edwards et al. |
| RE35,330 E | 9/1996 | Malone et al. |
| 5,556,396 A | 9/1996 | Cohen et al. |
| 5,569,242 A | 10/1996 | Lax et al. |
| 5,569,245 A | 10/1996 | Guglielmi et al. |
| 5,569,462 A | 10/1996 | Martinson et al. |
| 5,581,487 A | 12/1996 | Kelly et al. |
| 5,589,176 A | 12/1996 | Seare, Jr. |
| 5,598,848 A | 2/1997 | Swanson et al. |
| 5,601,600 A | 2/1997 | Ton |
| 5,605,693 A | 2/1997 | Seare, Jr. |
| 5,617,319 A | 4/1997 | Arakawa et al. |
| 5,632,767 A | 5/1997 | Sinofsky |
| 5,635,482 A | 6/1997 | Bhatnagar |
| 5,643,253 A | 7/1997 | Baxter et al. |
| 5,643,257 A | 7/1997 | Cohen et al. |
| 5,649,924 A | 7/1997 | Everett et al. |
| 5,658,282 A | 8/1997 | Daw et al. |
| 5,673,704 A | 10/1997 | Marchlinski et al. |
| 5,681,572 A | 10/1997 | Seare, Jr. |
| 5,743,905 A | 4/1998 | Eder et al. |
| 5,746,769 A | 5/1998 | Ton et al. |
| 5,785,705 A | 7/1998 | Baker |
| 5,785,706 A | 7/1998 | Bednarek |
| 5,800,529 A | 9/1998 | Brauker et al. |
| 5,810,810 A | 9/1998 | Tay et al. |
| 5,827,269 A | 10/1998 | Saadat |
| 5,830,222 A | 11/1998 | Makower |
| 5,836,875 A | 11/1998 | Webster, Jr. |
| 5,836,990 A | 11/1998 | Li |
| 5,891,457 A | 4/1999 | Neuwirth |
| 5,935,137 A | 8/1999 | Saadat et al. |
| 5,954,715 A | 9/1999 | Harrington et al. |
| 5,979,446 A | 11/1999 | Loy |
| 6,013,075 A | 1/2000 | Avramenko et al. |
| 6,042,590 A | 3/2000 | Sporri et al. |
| 6,059,779 A | 5/2000 | Mills |
| 6,066,139 A | 5/2000 | Ryan et al. |
| 6,068,626 A | 5/2000 | Harrington et al. |
| 6,071,283 A | 6/2000 | Nardella et al. |
| 6,080,152 A | 6/2000 | Nardella et al. |
| 6,091,995 A | 7/2000 | Ingle et al. |
| 6,096,052 A | 8/2000 | Callister et al. |
| 6,117,070 A | 9/2000 | Akiba |
| 6,145,505 A | 11/2000 | Nikolchev et al. |
| 6,176,240 B1 | 1/2001 | Nikolchev et al. |
| 6,178,354 B1 | 1/2001 | Gibson |
| 6,255,593 B1 | 7/2001 | Reede |
| 6,264,653 B1 | 7/2001 | Falwell |
| 6,309,384 B1 | 10/2001 | Harrington et al. |
| 6,346,102 B1 | 2/2002 | Harrington et al. |
| 6,391,024 B1 | 5/2002 | Sun et al. |
| 6,401,719 B1 | 6/2002 | Farley et al. |
| 6,432,116 B1 | 8/2002 | Callister et al. |
| 6,526,979 B1 | 3/2003 | Nikolchev et al. |
| 6,544,236 B1 | 4/2003 | Cragg et al. |
| 6,565,557 B1 | 5/2003 | Sporri et al. |
| 6,569,160 B1 | 5/2003 | Goldin et al. |
| 6,595,989 B1 | 7/2003 | Schaer |
| 6,634,361 B1 | 10/2003 | Nikolchev et al. |
| 6,637,962 B1 | 10/2003 | Roche et al. |
| 6,679,266 B2 | 1/2004 | Nikolchev et al. |
| 6,682,477 B2 | 1/2004 | Boebel et al. |
| 6,684,884 B2 | 2/2004 | Nikolchev et al. |
| 6,705,323 B1 | 3/2004 | Nikolchev et al. |
| 6,709,667 B1 | 3/2004 | Lowe et al. |
| 6,712,810 B2 | 3/2004 | Harrington et al. |
| 6,726,682 B2 | 4/2004 | Harrington et al. |
| 6,763,833 B1 | 7/2004 | Khera et al. |
| 6,780,182 B2 | 8/2004 | Bowman et al. |
| 6,871,085 B2 | 3/2005 | Sommer |
| 6,871,650 B1 | 3/2005 | Nikolchev et al. |
| 6,964,274 B1 | 11/2005 | Ryan et al. |
| 6,972,018 B2 | 12/2005 | Ryan et al. |
| 7,073,504 B2 | 7/2006 | Callister et al. |
| 7,195,630 B2 | 3/2007 | Ciarrocca |
| 7,220,259 B2 | 5/2007 | Harrington et al. |
| 7,237,552 B2 | 7/2007 | Khera et al. |
| 7,398,780 B2 | 7/2008 | Callister et al. |
| 7,428,904 B2 | 9/2008 | Nikolchev et al. |
| 7,500,974 B2 | 3/2009 | Sartor |
| 7,506,650 B2 | 3/2009 | Lowe et al. |
| 7,582,085 B2 | 9/2009 | Bowman et al. |
| 7,635,382 B2 | 12/2009 | Pryor |
| 7,699,056 B2 | 4/2010 | Tran et al. |
| 7,842,035 B2 * | 11/2010 | Harrington et al. ............. 606/50 |
| 7,905,880 B2 | 3/2011 | Harrington et al. |
| 8,100,129 B2 | 1/2012 | Swann |
| 2002/0177855 A1 | 11/2002 | Greene et al. |
| 2002/0188195 A1 | 12/2002 | Mills |
| 2002/0188247 A1 | 12/2002 | Peery |
| 2003/0032936 A1 | 2/2003 | Lederman |
| 2004/0186423 A1 | 9/2004 | Cafferata |
| 2004/0225187 A1 | 11/2004 | Kamrava et al. |
| 2004/0255958 A1 | 12/2004 | Harrington et al. |
| 2004/0267308 A1 | 12/2004 | Bagaoisan et al. |
| 2005/0045184 A1 | 3/2005 | Khera et al. |
| 2005/0143817 A1 | 6/2005 | Hunter et al. |
| 2005/0171402 A1 | 8/2005 | Cohen et al. |
| 2006/0116635 A1 | 6/2006 | Van Heugten et al. |
| 2006/0293560 A1 | 12/2006 | Nguyen et al. |
| 2007/0123781 A1 | 5/2007 | Callahan et al. |
| 2007/0135830 A1 | 6/2007 | Schaeffer |
| 2007/0161957 A1 | 7/2007 | Guenther et al. |
| 2007/0173883 A1 | 7/2007 | Keegan et al. |
| 2007/0196158 A1 | 8/2007 | Roche et al. |
| 2007/0215163 A1 | 9/2007 | Harrington et al. |
| 2008/0135053 A1 | 6/2008 | Gruber et al. |
| 2008/0167664 A1 | 7/2008 | Payne et al. |
| 2008/0249362 A1 | 10/2008 | Jiang et al. |
| 2009/0036840 A1 | 2/2009 | Viray et al. |
| 2009/0056722 A1 | 3/2009 | Swann |

| | | | |
|---|---|---|---|
| 2009/0062611 | A1 | 3/2009 | Toyama |
| 2009/0125023 | A1 | 5/2009 | Stephen et al. |
| 2009/0132141 | A1 | 5/2009 | Hrovat et al. |
| 2009/0209951 | A1 | 8/2009 | Marrouche et al. |
| 2009/0266366 | A1 | 10/2009 | Swann et al. |
| 2009/0281558 | A1 | 11/2009 | Li |
| 2010/0063360 | A1 | 3/2010 | Harrington et al. |
| 2010/0198214 | A1 | 8/2010 | Layton, Jr. et al. |
| 2011/0040146 | A1* | 2/2011 | Harrington et al. ........... 600/104 |
| 2011/0087109 | A1 | 4/2011 | Swann |
| 2011/0146692 | A1 | 6/2011 | Callaghan et al. |
| 2011/0180073 | A1 | 7/2011 | Callaghan et al. |
| 2011/0202077 | A1 | 8/2011 | Chin et al. |
| 2011/0276070 | A1 | 11/2011 | Viray et al. |
| 2011/0308527 | A1 | 12/2011 | Harrington et al. |

FOREIGN PATENT DOCUMENTS

| | | |
|---|---|---|
| CA | 2182738 | 10/2000 |
| CN | 1692872 | 11/2005 |
| DE | 3917179 | 12/1989 |
| EP | 0 105 669 | 4/1984 |
| EP | 0 153 190 | 8/1985 |
| EP | 0 541 258 | 5/1993 |
| EP | 0 752 236 | 1/1997 |
| EP | 1 554 999 | 7/2005 |
| EP | 1 169 974 | 12/2005 |
| GB | 2 359 492 | 8/2001 |
| WO | WO96/40023 | 12/1996 |
| WO | WO96/40024 | 12/1996 |
| WO | 97/17030 | 5/1997 |
| WO | WO97/17030 | 5/1997 |
| WO | WO97/49345 | 12/1997 |
| WO | WO98/55046 | 12/1998 |
| WO | WO01/91834 | 12/2001 |
| WO | WO02/28311 | 4/2002 |
| WO | 2009/132141 | 10/2009 |

OTHER PUBLICATIONS

Coleman, The Foreign Body Reaction: A Chronic Inflammatory Response, 8 J. Biomed. Mater. Res. 199-211 (1974).

Conceptus Incorporated, Summary of Safety and Effectiveness Data, P020014, Nov. 4, 2002.

Kearney, Patent Cooperation Treaty Written Opinion, International Application No. PCT/US98/08111, Date of Mailing Feb. 22, 1999.

Neuwirth, Update on Transcervical Sterilization, 51 International Journal of Gynecology & Obstetrics, Suppl. 1, S23-28 (1995).

Phillips, Experimental Closure of Arteriovenous Fistula by Transcatheter Electrocoagulation, 115 Radiology 319-21 (May 1975).

Pollack, Wound Healing: A Review, 5:5 J. Dermatol. Surg. Oncol. 389 (May 1979).

Quinones Guerror, Tubal Electrocauterization Under Hysteroscopic Control, 7 Contraception 195-201 (Mar. 1973).

Quinones, Hysteroscopic Sterilization, 14 International Journal of Gynecology & Obstetrics 27-34 (1976).

Sahwi, The Leukocytic Response to an Intrauterine Foreign Body in the Rabbit, 22 Fertility and Sterility 398 (Jun. 1971).

Thompson, Vessel Occlusion with Transcatheter Electrocoagulation: Initial Clinical Experience, 133 Radiology 335-340 (Nov. 1979).

Tibbs, Wound Healing Following Radiation Therapy: A Review, 42 Radiology and Oncology 99-106 (1997).

Office Action mailed Oct. 10, 2006, U.S. Appl. No. 10/812,476, filed Mar. 29, 2004 In Re: Douglas C. Harrington, "Method & Apparatus for Tubal Occlusion".

Office Action mailed Nov. 14, 2006, U.S. Appl. No. 10/924,584, filed Aug. 24, 2004 In Re: Brett S. Bowman, "Catheter Placement Detection System & Operator Interface".

Office Action mailed Feb. 21, 2008, U.S. Appl. No. 10/812,476, filed Mar. 29, 2004 In Re: Douglas C. Harrington, "Method & Apparatus for Tubal Occlusion".

Office Action mailed Feb. 7, 2008, U.S. Appl. No. 10/924,584, filed Aug. 24, 2004 In Re: Brett S. Bowman, "Catheter Placement Detection System & Operator Interface".

Office Action mailed Jul. 31, 2007, U.S. Appl. No. 10/924,584, filed Aug. 24, 2004 In Re: Brett S. Bowman, "Catheter Placement Detection System & Operator Interface".

Extended EP Search Report, related European Application No. 10156384.9 mailed May 4, 2010, 5 pp.

International Search Report, corresponding PCT Application No. GB2011/050100 mailed Jul. 29, 2011, 4 pp.

International Search Report, related PCT Application No. PCT/US00/02046 mailed Apr. 13, 2000, 2 pp.

* cited by examiner

STERILIZATION DEVICE AND METHOD

FIELD OF THE INVENTION

This application relates to devices and methods for occluding body vessels such as the uterotubal junction, uterine isthmus, and fallopian tubes and, in particular, to devices and methods for female sterilization/permanent contraception.

BACKGROUND

It is sometimes desirable to close the fallopian tubes of a woman for sterilization purposes or for other medical related reasons. The use of a minimally invasive medical procedure to close the fallopian tubes is often preferred in comparison to more invasive surgical methods, such as tubal ligation. One such minimally invasive medical procedure involves using a catheter device to wound the epithelial lining of a fallopian tube and then deploying a single implant into a fallopian tube. The wounding of the epithelial lining of the fallopian tube will stimulate tissue ingrowth into the porous implant to fully occlude the fallopian tube in time, resulting in permanent sterilization.

An example of such a catheter device is the Adiana® Permanent Contraception system (Hologic, Inc., Marlborough, Mass.). To use this system, a flexible delivery catheter is passed through the vagina and cervix and into a fallopian tube to deliver a low level of radiofrequency energy, followed by the delivery of a small, compressible occlusion implant. An implant stored in the device is placed in the uterotubal junction of a fallopian tube to permanently occlude said fallopian tube. Such devices and procedures are described, for example, in U.S. Pat. No. 6,309,384, which is incorporated herein by reference in its entirety. This device, however, is generally adapted to effectuate occlusion of a single fallopian tube, thereby requiring employment of two such devices to effectuate occlusion of both fallopian tubes.

SUMMARY

In accordance with some embodiments, a device configured for insertion into a fallopian tube is shown and described. The device includes a distal end and a proximal end having a handle thereon, an external electrode sheath, an internal sheath, and a positioning member. The external electrode sheath has a lumen sized for housing a first porous implant at the distal end and is configured to slide distally and proximally along its long axis. Further, the external sheath has at least one ring electrode disposed about its outer diameter for wounding an epithelial layer of a fallopian tube. The internal sheath is longitudinally disposed within the lumen of the external electrode sheath at its distal end and has a lumen sized for housing a second porous implant. Alternatively, in some embodiments, the internal sheath could house both the first and second porous implants. The positioning member is slideably disposed within the lumen of the internal sheath proximal to the first and second porous implants along the long axis and is configured to slide toward the distal end of the catheter. Sliding at least one of the external electrode sheath or the positioning member relative to one another disposes the first porous implant within a first fallopian tube and disposes the second porous implant within a second fallopian tube.

In accordance with other embodiments, a device configured for insertion into a fallopian tube is shown and described. The device includes a distal end and a proximal end having a handle thereon, an external electrode sheath, and a positioning member. The external electrode sheath has a lumen sized for housing two porous implants along a long axis thereof and is configured to slide distally and proximally along its long axis relative to the handle. The positioning member is disposed within the lumen of the external electrode sheath proximal to the two porous implants along the long axis. Sliding the external electrode sheath toward the proximal end of the catheter disposes at least one of the two porous implants within a fallopian tube.

In accordance with other embodiments, a method for occluding two fallopian tubes using a single catheter containing two porous implants is shown and described. The method includes: (i) inserting a catheter into a first fallopian tube, wherein the catheter comprises: a distal end and a proximal end having a handle thereon; an external electrode sheath having a lumen sized for housing two porous implants at the distal end and along a long axis thereof, the external sheath having ring electrodes disposed about its outer diameter for wounding an epithelial layer of a fallopian tube; and a positioning member disposed within the lumen of the external electrode sheath proximal to the two porous implants along the long axis; (ii) wounding an epithelial layer of a first fallopian tube using the ring electrodes on the external electrode sheath; (iii) sliding the external electrode sheath toward the proximal end of the catheter to dispose a first porous implant within a first fallopian tube where wounding occurred. The method further comprises: (iv) removing the catheter from the first fallopian tube and inserting the catheter into a second fallopian tube; (v) wounding an epithelial layer of a second fallopian tube using the ring electrodes on the external electrode sheath; and (vi) sliding the external electrode sheath toward the proximal end of the catheter to dispose a second porous implant within a second fallopian tube where wounding occurred.

In accordance with other embodiments, a method for occluding two fallopian tubes using a single catheter containing two porous implants is shown and described, wherein both porous implants are housed within an internal sheath. The method includes: (i) inserting a catheter into a first fallopian tube, wherein the catheter comprises: a distal end and a proximal end having a handle thereon; an external electrode sheath having ring electrodes disposed about its outer diameter for wounding an epithelial layer of a fallopian tube; an internal electrode sheath housed within at least a portion of the external electrode sheath and defining an inner lumen sized for housing two porous implants at its distal end and along a long axis thereof; and a positioning member disposed within the lumen of the internal electrode sheath proximal to the two porous implants along the long axis; (ii) wounding an epithelial layer of a first fallopian tube using the ring electrodes on the external electrode sheath; (iii) sliding both the external and internal sheaths proximally to place a first porous implant in a loaded position; (iv) sliding the external sheath proximally to dispose the first porous implant within a first fallopian tube where wounding occurred. The method further comprises: (v) removing the catheter from the first fallopian tube; (vi) reloading the catheter by moving the external sheath distally and the internal sheath proximally to place a second porous implant in a ready to deploy position; (vii) inserting the catheter into a second fallopian tube; (viii) wounding an epithelial layer of a second fallopian tube using the ring electrodes on the external electrode sheath; and (ix) sliding the external electrode sheath toward the proximal end of the catheter to dispose a second porous implant within a second fallopian tube where wounding occurred.

BRIEF DESCRIPTION OF THE DRAWINGS

Illustrative and presently preferred embodiments of the invention are shown in the drawings, in which.

DETAILED DESCRIPTION

At the outset, female sterilization and/or permanent contraception devices and related methods are shown and described The sterilization devices generally include a handle component, which may be disposable at least in part, and a catheter component including a segment designed to wound a portion of the epithelial lining of each fallopian tube. At least two porous implants or plugs are stored in the catheter portion. The devices are adapted to wound a segment of a first fallopian tube, dispose an implant at the wounded segment, and then repeat the procedure in the second fallopian tube. Upon wounding and implantation, vascularized tissue grows into each implant and/or a vascularized plug forms around one or both implants, leading to total occlusion of both fallopian tubes and sterilization of the female patient.

Related catheters, porous implants, systems and methods for tubal occlusion and female sterilization, and devices for deploying implants using a catheter are described in: U.S. patent application Ser. No. 12/232,842, entitled "Atraumatic Ball Tip and Side Wall Opening"; U.S. patent application Ser. No. 11/752,222, entitled "Method and Apparatus for Tubal Occlusion"; U.S. patent application Ser. No. 10/812,476, entitled "Method and Apparatus for Tubal Occlusion"; U.S. patent application Ser. No. 11/562,882, entitled "Delivery Catheter with Implant Ejection Mechanism"; U.S. Pat. Nos. 7,582,085 and 6,780,182, both entitled "Catheter Placement Detection System and Operator Interface"; U.S. Pat. Nos. 7,220,259, 6,726,682, 6,712,810, 6,346,102, 6,309,384, 6,068,626, and 5,954,715, each entitled "Method and Apparatus for Tubal Occlusion; U.S. Pat. No. 5,681,572, entitled "Porous Material Produce and Process"; and U.S. Pat. No. 5,095,917, entitled "Transuterine Sterilization Apparatus and Method"; all of which are incorporated herein by references in their entireties as part of the present disclosure.

Figure 1:
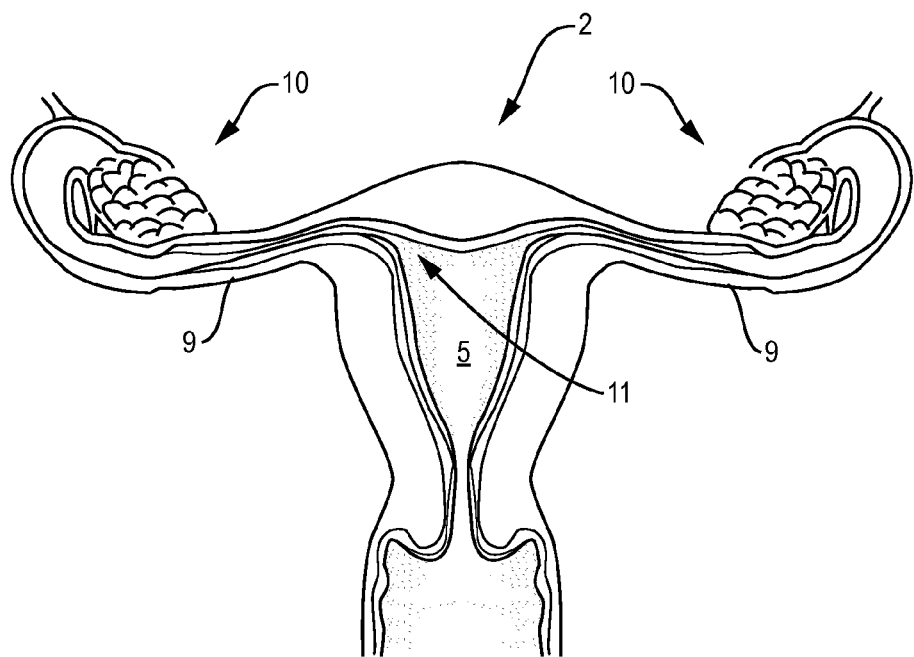
FIG. 1 is a partial view of a female reproductive system.
Figure 2:
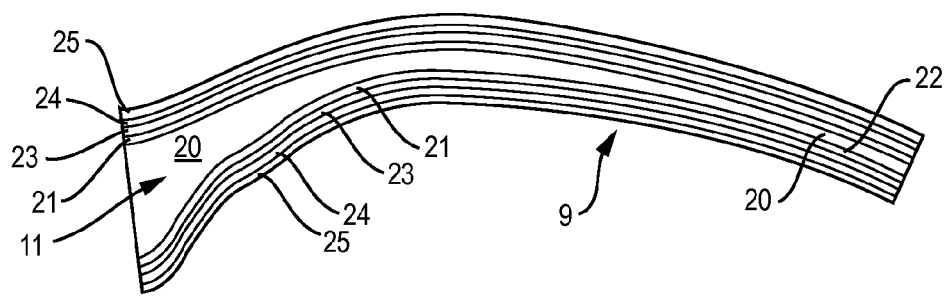
FIG. 2 is a cross-sectional view of the uterotubal junction of the female reproductive system.

By way of background, FIGS. 1 and 2 generally illustrate the female uterus and fallopian tubes in which the devices and methods described herein may be utilized. The devices incorporate a catheter segment that is designed and intended to create a uniform lesion along a short length of the ovarian pathways of a female patient. To help illustrate the intended area of use of the device, FIG. 1 shows some of the major elements of the female reproductive system. The uterus 2 consists of a cavity referred to as the uterine cavity 5. The fallopian tube (or ampulla) 9 is a hollow organ that connects the uterus 2 to the ovary 10. The site where the fallopian tube 9 and uterus 2 connect is called the uterotubal junction 11. The uterotubal junction 11 is where the porous implants described herein are disposed after wounding. The uterotubal junction 11 is a section of tubular shape of about 10 mm in length (in the resting position) or up to about 2 mm in length when gas or liquid is pushed through the uterus and fallopian tubes. The uterotubal junction 11 provides a transition between the uterus 2 and the fallopian tube 9, and the area of transition from the chamber of the uterus 2 to the lumen of the uterotubal junction 11 is referred to as the ostium or cornu.

The FIG. 2 cross section shows the layers of tissue that make up the uterotubal junction 11. The treatment methods described herein necessarily include appreciating the extent to which each of these layers of tissue are damaged prior to insertion of a porous implant. A more detailed description of these layers of tissue and the depth of tissue wounding are described in U.S. Patent App. Pub. No. 2002/0255958, filed on Dec. 23, 2004, which is incorporated herein by reference for all that it discloses. By way of brief discussion of these layers of tissue, the lumen 20 passes through the fallopian tube, and this lumen is lined with a layer of mucosal tissue consisting of epithelium 21 and lamina propria 23. Within the fallopian tube, this layer of mucosal tissue is referred to as the endosalpinx 22. The layer of tissue under the epithelial layer is the lamina propria 23, which is surrounded by a layer of circular muscle 24, which is surrounded by layer of longitudinal muscle 25.

Figure 3:
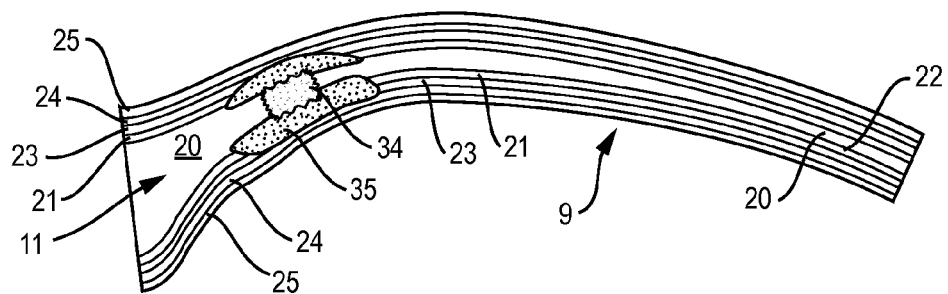
FIG. 3 is a cross-sectional view of the uterotubal junction of the female reproductive system with a porous implant in place.

FIG. 3 illustrates the desired degree of damage in each of the tissue layers of the uterotubal junction 11, and the desired interaction between the tissue and the porous implant 34 which is inserted to generate an occlusion of the fallopian tube. The porous foam matrix, also called a plug, or implant 34, is inserted into the target site for occlusion, which in this illustration is the uterotubal junction 11. The porous implant 34 is put in place after the target site has been treated or wounded by application of thermal RF energy. The thermal RF energy is delivered at levels well below the level required to cause a severe burn (and the concomitant severe inflammatory response), but sufficient to cause thermal necrosis of the epithelial layer 21 and the lamina propria 23. The area of thermal death (necrosis) is indicated as item 35, and extends for a length of approximately 4 to 10 millimeters along the pathway. Damage to the circular muscle layer 24 is acceptable, but damage to the longitudinal muscle layer 25 is undesirable. This may lead to minimal collapse of the uterotubal junction about the implants.

The wounded area of the uterotubal junction responds with a normal "wound healing response." The term "wound healing response" is a term understood in the art to include biological activities including: (1) arrival of leukocytes, neutrophils, monocytes, and their transformation into macrophages and aggregation into giant cells, and arrival of fibroblast cells, (collectively referred to as inflammatory cells), and (2) the creation of an extracellular matrix and deposition of proteins, and (3) the formation of granulation and connective tissue at the wound site. Further details of the tissue wound healing response as it relates to the architecture of the implants are described in the above-referenced U.S. Patent App. Pub. No. 2002/0255958, filed on Dec. 23, 2004, which is incorporated herein by reference for all that it discloses.

To facilitate wounding and occlusion, a catheter or like device is inserted into the uterus transcervically, and the distal tip of the catheter is navigated into the ovarian pathways, until the wounding segment is stationed at the desired point along the ovarian pathway, such as at the uterotubal junction, which provides a good location for wounding and porous implant placement. Physicians may view the placement with an endoscope or hysteroscope, and/or placement within the pathway can be confirmed with fluoroscopy or ultrasound or other imaging modality to detect a radiopaque implant. Alternatively, placement of the catheter may be accomplished blindly, using tactile feedback only. Once the wounding element is in place, the appropriate wound may be created by application of power limited so as to destroy the epithelial layer/endosalpinx in the area of porous implant placement, while avoiding unwanted physiological reactions.

Figure 5:
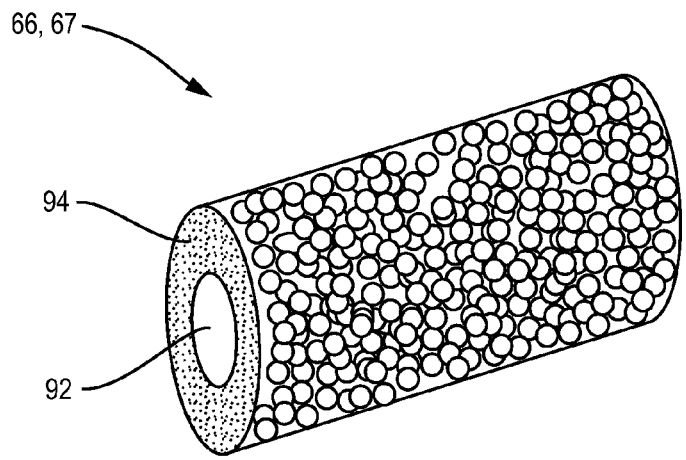
FIG. 5 is a perspective view showing a cross-section of an occlusive implant that may be delivered into a patient, using the delivery devices described herein.
Figure 6:
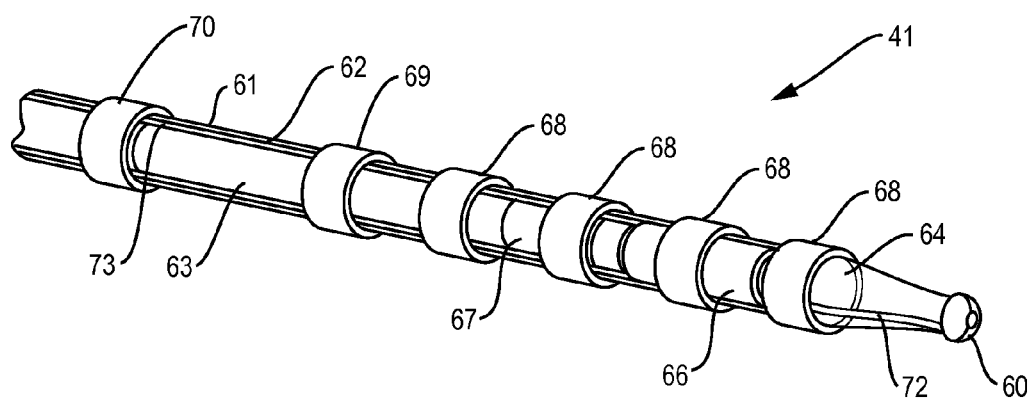
FIG. 6 is a perspective view of a distal tip of the sterilization device of FIG. 4.
Figure 7:
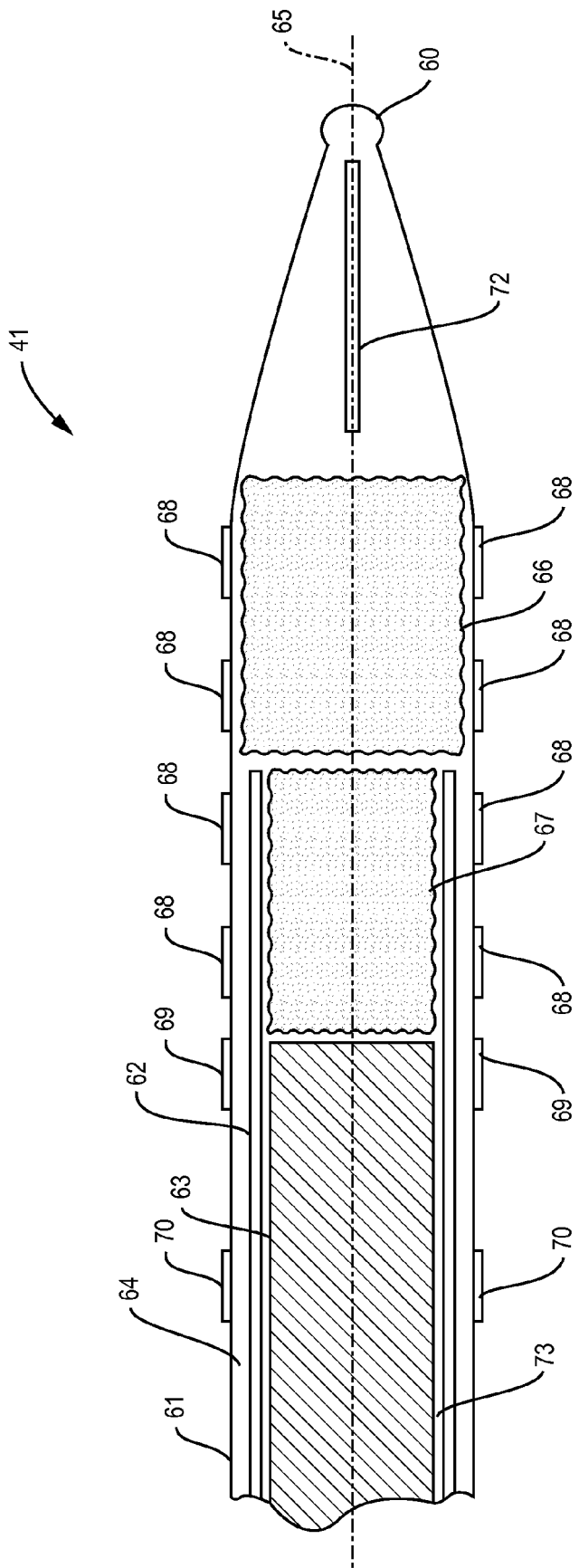
FIG. 7 is a cross-sectional view of a distal tip of the sterilization device of FIG. 4 having two porous implants housed therein.
Figure 8:
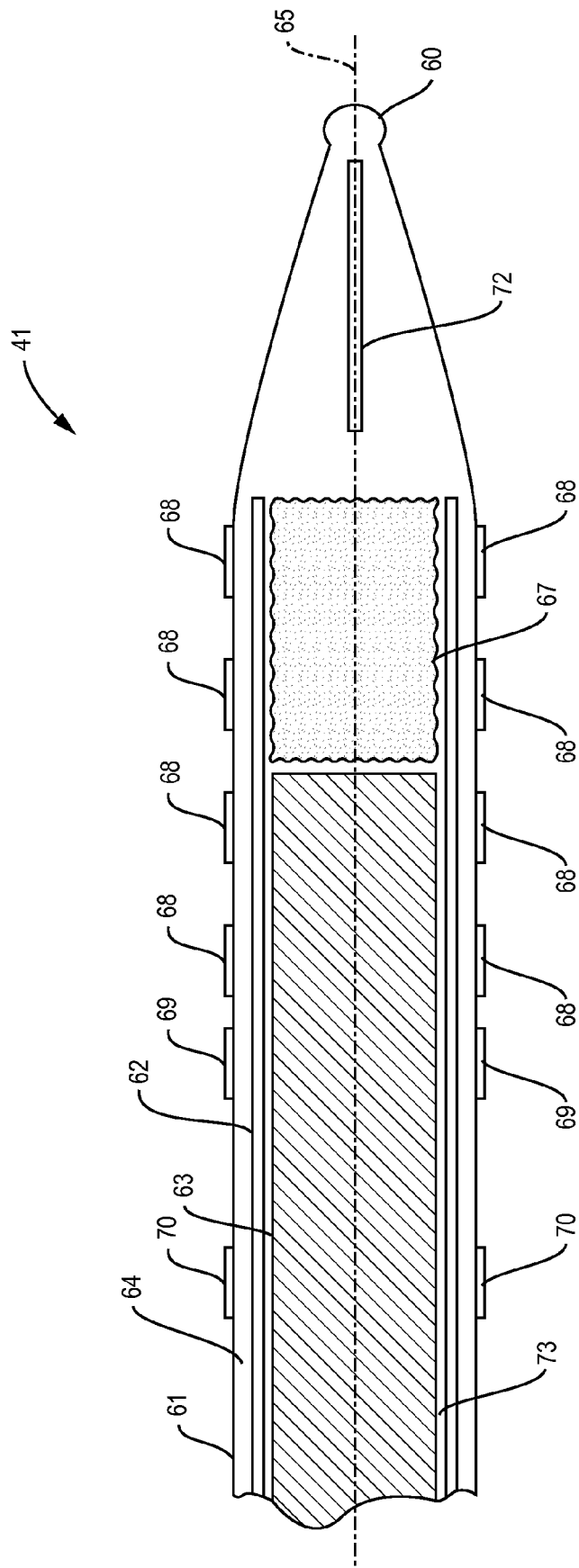
FIG. 8 is a cross-sectional view of the distal tip of the sterilization device of FIG. 4 having one remaining porous implant residing within the inner sheath (after deployment of the first porous implant)
Figure 9:
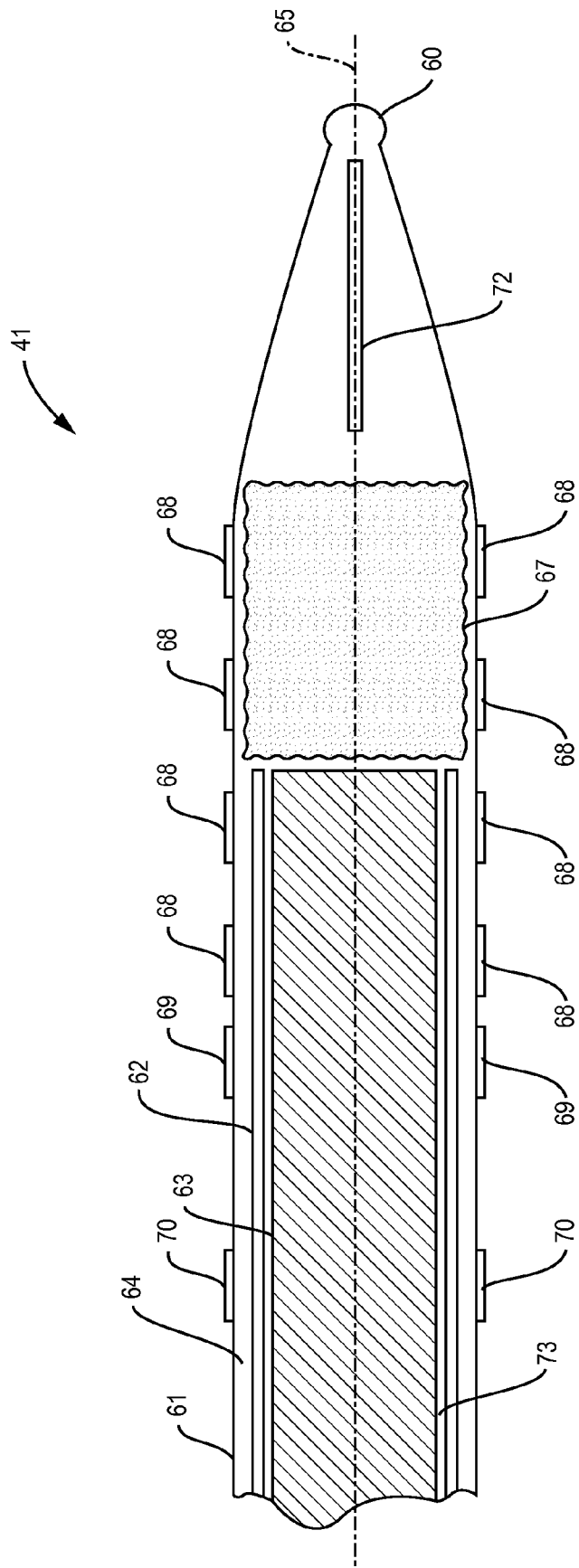
FIG. 9 is a cross-sectional view of the distal tip of the sterilization device of FIG. 4 having one remaining porous implant residing outside of the inner sheath (after deployment of the first porous implant and retraction of the inner sheath)

The porous implants described herein may be formed as an elongated porous foam matrix or plug and are disposed longitudinally within the external sheath lumen 61 and/or the internal sheath lumen 62 (shown in FIGS. 7-9). The porous implants (shown as 66-67 in FIGS. 5-9) are preferably made from a material with a pore size, chemistry and architecture that actually facilitates cellular ingrowth into the material over time, eventually fully occluding the ovarian pathways. Once both ovarian pathways are fully occluded, any eggs released by the ovaries will be prevented from reaching the uterus and any sperm cells released into the uterine cavity will be prevented from contacting said eggs; hence, contraception is achieved. The porous implants 66-67 may be formed of silicone and/or a radiopaque material so that the implants may be visible under different imaging modalities to verify placement of the porous implants. In one embodiment, shown in FIG. 5, the porous implants 66-67 comprise an inner matrix or core 92 surrounded by an outer matrix or layer 94. In a further embodiment, the outer matrix 94 is approximately 100% Silicon, while the inner matrix is, by volume, approximately 85% Silicon and approximately 15% Tantalum; although the amount of Tantalum, by volume, could range from about 5% to about 40%.

Silicone foam is readily formed into porous implants with the procedure set forth in Seare, Method of Marking a Porous Implant, U.S. Pat. No. 5,605,693 (Feb. 25, 1997), which is incorporated herein by reference for all that it discloses. The porous implants 66-67 may be formed of large pore foam, and in some examples, may have pore sizes averaging approximately 40 to 200 microns. The overall length of the implants 66-67 typically ranges from about 2 mm to about 10 mm and, more preferably, from about 3 mm to about 5 mm. Further detailed description of the porous implants 66-67 contemplated herein can be found in U.S. Publication No. 2004/0255958, filed Mar. 29, 2004, which is incorporated herein by reference for all that it discloses.

The catheter component ("catheter") 47 of the device 40 contains two porous implants (best shown in FIG. 5 as 66-67), one for occluding each fallopian tube. Having two implants effectively streamlines this minimally invasive medical procedure for patients seeking permanent contraception by allowing the procedure to be performed on both fallopian tubes using a single device 40, as opposed to performing the procedure using a separate device for each fallopian tube. The catheter 47 may be inserted into a first ovarian pathway or fallopian tube at a desired target site, such as the uterotubal junction 11. Once the catheter 47 is in place at the first uterotubal junction 11, a physician operates the catheter 47 to cause wounding and then deployment of a first porous implant 66. The catheter 47 is then removed from the first uterotubal junction 11 (typically using a hysteroscope), reloaded (typically while the catheter is in the uterine cavity or otherwise within the hysteroscope's working channel), and then inserted into the second uterotubal junction 11. Once the catheter 47 is in place at the second uterotubal junction 11, the physician operates the catheter 47 to cause wounding and then deployment of a second porous implant 67. The operation of the distal end 41 of catheter 47 containing the two porous implants 66-67 will be described in further detail below.

FIGS. 4-9 illustrate a sterilization device 40 configured for insertion into a fallopian tube. The sterilization device 40 has a handle component ("handle") 43 about its proximal end 42 configured for manipulation by hand, and has a catheter component ("catheter") 47 on its distal end configured for insertion into a patient through the cervical canal, uterus, and into the uterotubal junction. The distal end 41 of catheter 47 of sterilization device 40 is necessarily a narrow tube having an outer diameter between about 0.5 mm and about 2 mm and, in one embodiment, has an outer diameter of about 1.3 mm, and a length between about 5 mm and about 20 mm, and in one embodiment, has a length of about 8 mm. The overall length of the catheter 47 is generally between about 25 cm and about 75 cm and, in one embodiment, the length of the catheter is about 50 cm. The distal end 41 of the catheter 47 houses at least one porous implant therein. In the embodiments shown in FIGS. 6-9, the distal end 41 houses two porous implants therein for occluding each of a woman's fallopian tubes. It is also contemplated that more than two porous implants may be included within the distal end 41 taught herein.

In operation, the physician holds the handle component 43 of the sterilization device 40 to control positioning of the distal end 41 of the catheter 47 with visual assistance provided by a hysteroscope. Proper placement of the distal end 41 of catheter 47 within the ovarian pathway is important, and is ensured with four circumferentially spaced pad electrodes 69, also referred to as the position detection electrodes 69 (best shown in FIGS. 6-9). The pad electrodes 69 are used in conjunction with a user interface, such as the control box 50 shown in FIG. 4, to inform the physician when proper placement has been achieved. Although four pad electrodes are typically employed, it should be noted that the catheter could include any number of pads ranging from 1-3 pads to a number of pads greater than four. The four pad electrodes 69 are placed around the outer circumference of the catheter toward the distal end 41 to form a position detection array (PDA).

Figure 4:
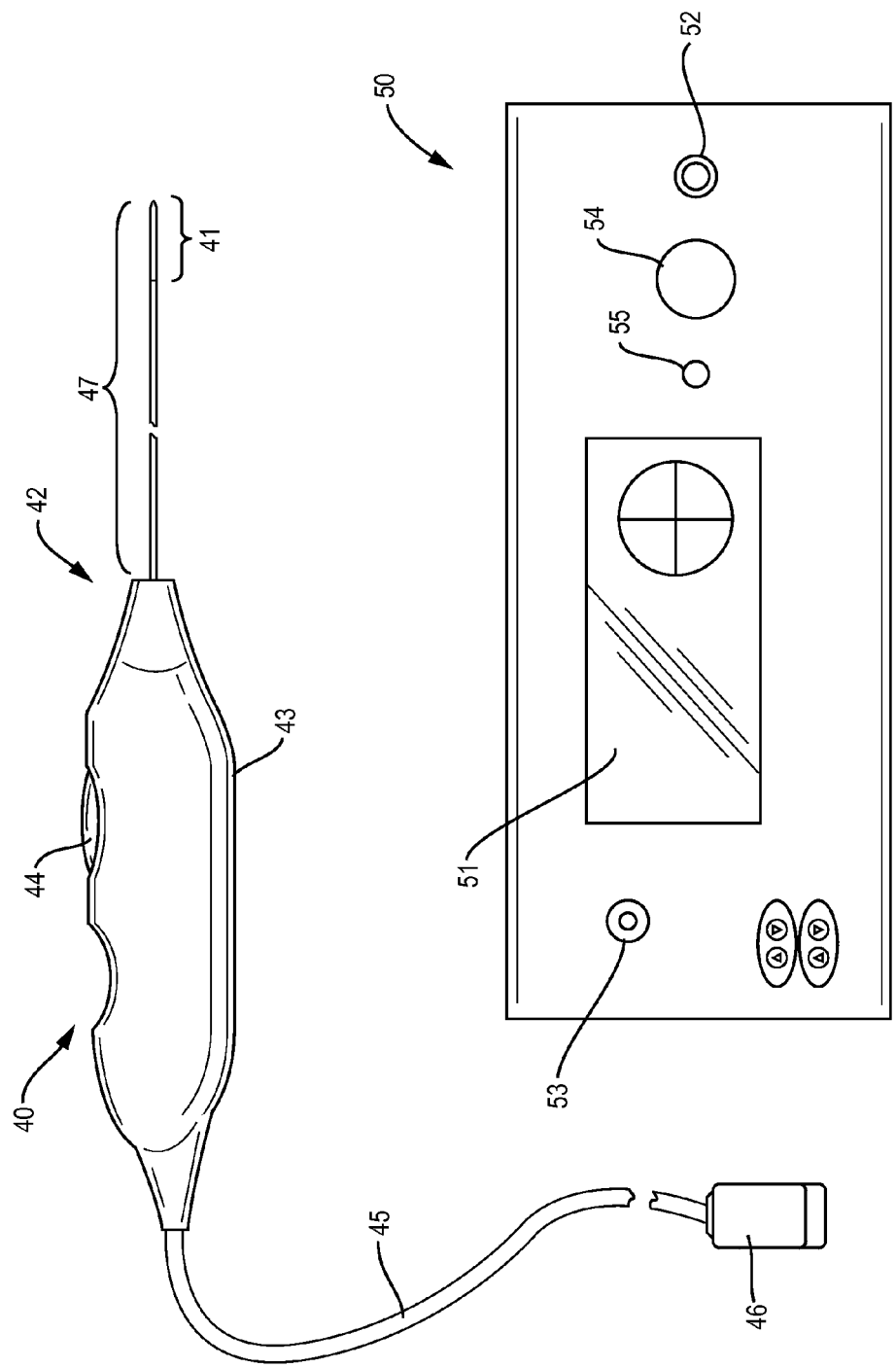
FIG. 4 is a perspective view of a sterilization device and control box.

With continued reference to FIG. 4, the device 40 may include a manually engageable member, such as a push button 44, which gives the user manual control over one or more of the device's functions, such as, for example, control over the deployment of the porous implants 66-67. Electrical wires which supply RF power to the four ring electrodes 68 (described below) on the distal tip 41 of the catheter 47 may run through the lumen of the catheter body or may be housed within the catheter body. An electrical connector 46 is supplied on the proximal end 42 of the device 43 to connect the wires in the catheter to the RF power supply of the control box 50 via cable 45. The cable 45 terminates in an electrical connector 46 designed to be received by a power and signal connector 52 on the control box 50. The cable 45 is provided in a length that allows for convenient placement of the control box 50 with respect to a patient, and may typically be three to 10 feet in length. The sterilization device 40 must be sterile and thus may be a disposable component, while the control box 50 may remain outside of the sterile field and may be reusable.

The control box 50 houses electronics and a computer system for interpreting signals from the RF and PDA electrodes 68-69, both on the catheter distal tip 41, controlling movement of the internal components to deploy the porous implants 66-67, driving the display 51, receiving operator input, and controlling the catheter 47 and distal end 41 accordingly.

The control box 50 further serves as a user interface and includes an interface display 51 and a power and signal connector 52, which is designed to mate with connector 46 on sterilization device 40. The power and signal connector 52 provides impedance measuring signals and treatment power to the distal tip 41 of catheter 47 of the sterilization device 40, and receives impedance signals from the position detection electrodes 69. A main power switch 53 controls power to the control box 50 for powering the display 51 indicator lights, any desired audio signals, and the distal end 41 of catheter 47. A catheter power switch 54 controls the provision of treatment power to the treatment electrodes 68. Further controls may also be provided on the control box 50, such as a reset switch 55 for re-initiation of the system.

FIGS. 6-9 illustrate an embodiment of the distal operating end or portion 41 of the catheter 47 shown in FIG. 4. The distal portion 41 of the catheter 47 includes an external electrode sheath 61, an internal sheath 62, a positioning member 63, such as a push-rod, a first implant 66, and a second implant 67. The external electrode sheath 61, internal sheath 62 and positioning member 63 are concentrically nested and share the same longitudinal axis 65. The distal portion 41 of the external electrode sheath 61 tapers or narrows to terminate in an atraumatic ball tip 60 to prevent inadvertent uterine or fallopian tube punctures. In some implementations, the catheter 47 may also include an additional external sheath (not shown) or introducer to help protect the most distal end 41 of the catheter 47 for insertion through instruments, vessel lumens, and/or body cavities. The external electrode sheath 61 has a lumen 64 disposed along a long axis 65 sized for housing a first porous implant 66. The external sheath 61 has four axially spaced ring electrodes 68, each disposed circumferentially around the sheath's outer surface, and may also include temperature and/or impedance sensors and electrically conductive wires to couple the electrodes and/or temperature or impedance sensors with the control box 50. The four ring electrodes 68 form the RF electrode bands or RF electrode array. Further, as previously indicated, the external sheath 61 includes four electrode pads 69 circumferentially spaced around the sheath's outer surface and forming a position detection array (PDA). Optionally, at least one optical member 70, shown as a ring member on the distal portion 41 of the external sheath 61, may be included to assist the user in visually tracking the distal portion 41 of the catheter and/or external electrode sheath 61 as it is inserted into the patient.

For example, in procedures where a hysteroscope is used in conjunction with the sterilization device 40 to guide the device into the uterus, the optical member 70 allows the user to determine when the distal portion 41 of the catheter 47 has entered the uterotubal junction 11. Though not required, the optical member 70 could include one or more radiopaque features either externally and/or integrated within its own composition to enhance or allow its visibility in one or more imaging modalities that are currently known or that later become known, for example x-ray, ultrasound, MRI (magnetic resonance imaging), CT (computed tomography), Nuclear Medicine, Fluoroscopy, etc.

A longitudinal slit 72 is disposed in the distal tip 41 of the external sheath 61 and has an opening sized to allow the porous implants 66-67 to exit therethrough. In one embodiment, the length of the slit 72 may be approximately 3 mm; however the length of the slit can range from approximately 2 mm to approximately 20 mm. While the slit 72 is shown and described in FIG. 7 as being longitudinal, other configurations are also possible. The slit 72 may have a number of other shapes or sizes, such as being in the shape of a letter "M", for example. The external sheath 61 is configured to slide distally and proximally along a long axis 65 to reveal the porous implant (when slid proximally 42) or to reshroud the internal sheath 62 (when slid distally 41).

In one exemplary configuration, the distal end of catheter 41 has an internal sheath 62 longitudinally disposed within the lumen 64 of the external sheath 61 at its distal end 41 and is configured to remain stationary with regard to the handle 43. The internal sheath 62 has a lumen 73 sized for housing a second porous implant 67 along the long axis 65. The internal sheath 62 is positioned proximally to first porous implant 66 and may help, at least in part, to deploy the first implant 66 (as will be described in further detail below).

As shown in FIG. 7, the first porous implant 66 is positioned distal to the second porous implant 67, allowing for the first porous implant 66 to be disposed first, followed by the second porous implant 67. As also shown in FIG. 7, the first and second porous implants 66-67 are positioned adjacent one another and may be longitudinally disposed with regard to the long axis 65. In alternative embodiments, the first and second porous implants 66 and 67 may not be directly adjacent to one another and may offset with respect to the long axis 65.

A positioning member 63, such as a push rod, is slideably disposed within the lumen 73 of the internal sheath 62 proximal to the second porous implant 67 along the long axis 65. The positioning member 63 is configured to slide toward the distal ball tip 60 end of the catheter distal tip 41 to, at least in part, push the second porous implant 67 toward the slit 72. Sliding at least one of the external electrode sheath 61 or the positioning member 63 relative to one another disposes the first porous implant 66 within a first fallopian tube and disposes the second porous implant 67 within a second fallopian tube, as will be described below in further detail.

In an alternative embodiment, the distal end 41 of the catheter 47 may be formed of an external electrode sheath 61 and positioning member 63 without the need for an internal sheath 62. In this configuration, both porous implants 66-67 could simply be housed within the lumen 64 of the external electrode sheath 61. Sliding the external electrode sheath 61 proximally or sliding the positioning member 63 distally would result in deployment of one or both of the porous implants 66-67 at the desired location. In this embodiment, the second porous implant 67 may, at least partially, push the first porous implant 66 toward the slit 72 to release it from the catheter.

Once wounding of a first fallopian tube has occurred, the external electrode sheath 61 is slid proximally to dispose the first porous implant 66 within the first fallopian tube at the position where wounding occurred. When the external electrode sheath 61 is retracted, or slid proximally along the longitudinal axis 65, the internal sheath 62 and positioning member 63 remain stationary, forcing the first porous implant 66 toward and into the distal ball tip 60 and out of the slit 72. The retraction of the external electrode sheath 61 allows the porous implant to be disposed within the fallopian tube at the exact position where wounding occurred, thus facilitating tissue ingrowth into the porous implant. After deployment of the first porous implant 66 (and proximal retraction of the external electrode sheath 61) the internal sheath 62 and/or positioning member 63 may be protruding slightly from slit 72 and, therefore, may need to be reshrouded to prepare the distal end 41 of catheter 47 for the deployment of the second porous implant 67.

FIG. 7 illustrates the distal end 41 prior to deployment of the first porous implant 66. FIGS. 8-9 together illustrate the reshrouding or reloading that must occur to prepare the second porous implant 67 for deployment after deployment of the first porous implant 66. FIG. 8 illustrates the distal end 41 after deployment of the first porous implant 66, as the external electrode sheath 61 has just begun to slide toward the distal end 41, reshrouding the internal sheath. However, in FIG. 8, the positioning member 63 has not yet started to slide distally so the second porous implant 67 is still housed within the internal sheath 62 and is not yet in position to deploy. In some embodiments, the external electrode sheath 61 and positioning member 63 may slide distally simultaneously, in other embodiments either the external electrode sheath 61 or the positioning member 63 may begin to move before the other.

After the first porous implant 66 has been deployed, the external electrode sheath 61 slides toward the distal end 41 to reshroud the internal sheath, while the positioning member 63 also slides toward the distal end 41 to push the second porous implant 67 distally and position it for deployment, as shown in FIG. 9. In some embodiments, the external electrode sheath 61 and positioning member 63 may be sliding distally simultaneously. In this position, shown in FIG. 9, the second porous implant 67 is pushed out of the internal sheath 62 and thus is housed within the distal end 41 of external electrode sheath 61, now ready for deployment. The total length that the electrode sheath 61 travels and/or slides (proximally and distally) is within the range of about 5 mm to about 25 mm and, in some embodiments, the electrode sheath travels and/or slides between about 10 mm and about 15 mm. The positioning member 63 travels and/or slides between about 2 mm and about 10 mm and, in some embodiments, the positioning member 63 travels and/or slides between about 4 mm and about 5 mm. The reshrouding of the internal sheath 62 and distal movement of the second porous implant 67 to reload the device (i.e. position the next implant in a ready to deploy position) may be accomplished very quickly, often in about a second (or in a matter of milliseconds), and typically occurs within the patient's uterine cavity, fallopian tube and/or within the working channel of a hysteroscope or endoscope (if a hysteroscope or endoscope are used during the procedure) while the physician is substantially simultaneously removing the distal end 41 of the catheter 47 from the first fallopian tube and inserting it into the second fallopian tube.

Once the distal end 41 of the catheter 47 is in place and wounding has occurred, the external electrode sheath 61 is again retracted proximally to dispose the second porous implant 67 within the second fallopian tube at the position where wounding occurred. When the external electrode sheath 61 is retracted the internal sheath 62 and positioning member 63 will remain stationary (relative to the handle 43) to force the second porous implant 67 toward the distal ball tip 60 and out of the slit 72. The operation of retracting the external electrode sheath 61 while keeping the internal sheath 62 and positioning member 63 stationary may be the same for both deployments (of the first and second porous implants 66-67).

In one embodiment, the first porous implant 66, may be forced toward the slit 72 (while retracting external electrode sheath 61), at least partially, by the second porous implant 67. In another embodiment, the first porous implant 66, may be forced toward the slit 72 (while retracting external electrode sheath 61), at least partially, by the positioning member 63. In some embodiments described herein, the internal sheath 62 remains stationary (relative to the handle 43) while the positioning member 63 slides distally and the external electrode sheath 61 slides proximally and distally along the long axis 65 to either dispose/reveal the porous implants or reshroud and/or position the porous implants in preparation for deployment.

The movement of the external electrode sheath 61 and positioning member 63 may be controlled by a number of different method, and may be controlled or driven using one or a combination of mechanical components, electrical components, or computer software. For example, the external electrode sheath 61 and positioning member 63 may be electrically or mechanically controlled, such as by a linear actuator, a stepper motor having a shaft operating reciprocally, a rotating four-bar linkage mechanism, a rack and pinion mechanism, or a biasing member, such as a leaf-type or other type of spring. The mechanisms controlling movement of the distal ends of external electrode sheath 61 and positioning member 63 may be located at the proximal end of the sterilization device 40, such as within the handle 43, control box 50, or both. The surgeon may control operation of the distal end 41 of the catheter 47 (and thus movement of the external electrode sheath 61 and positioning member 63) by a number of different mechanisms, such as a foot-pedal, switch on the control box 50, push button, or switch positioned on the handle 43. Alternatively, the deployment of the implants could be initiated by the computer control box automatically following successful delivery of RF energy.

Figure 10:
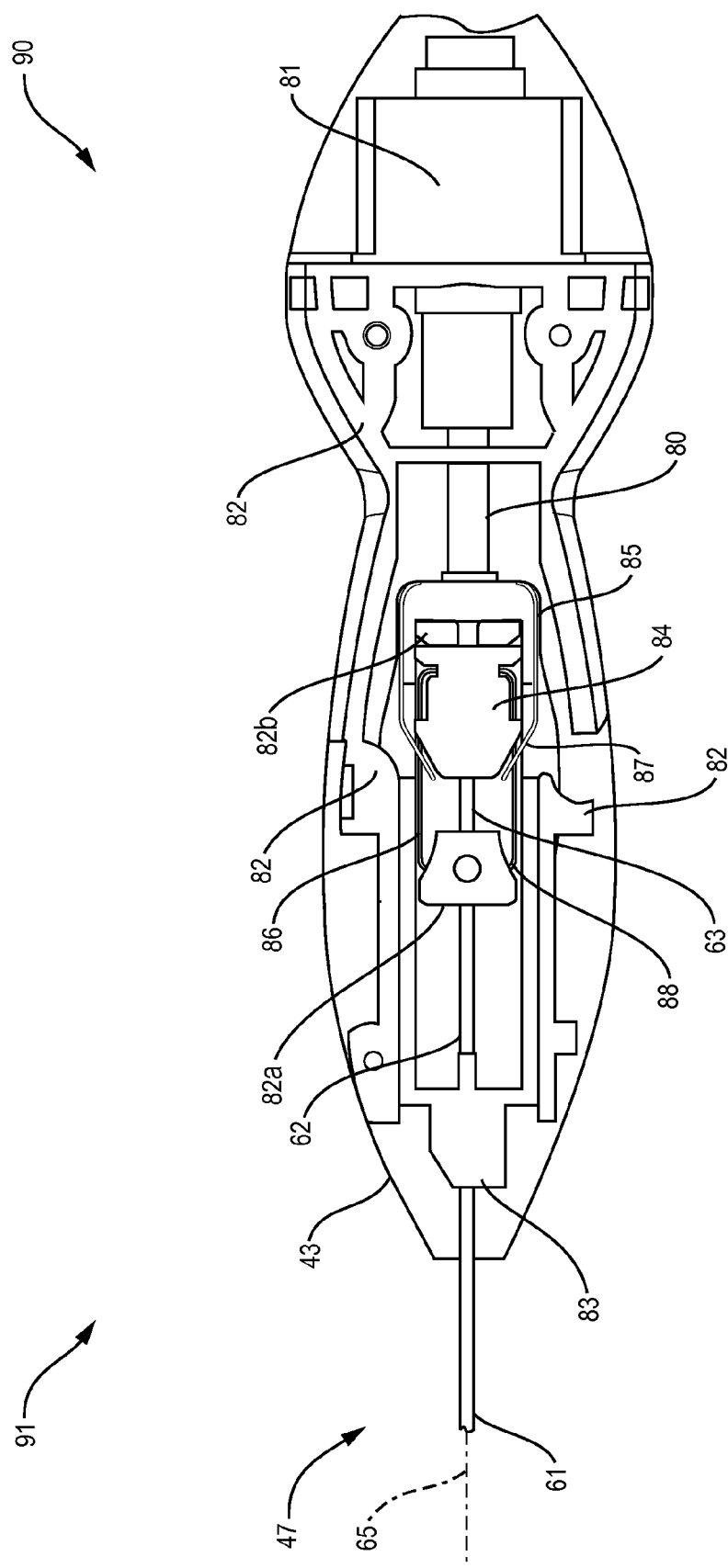
FIG. 10 is a cross-sectional bottom view of the handle of a sterilization device in a starting (pre-deployment) position.

In one embodiment, the sliding operations of the external electrode sheath 61 and positioning member 63 are controlled by a reciprocating shaft 80 within the handle 43, as shown in FIG. 10. The reciprocating shaft 80 slides back and forth toward the proximal 90 and distal 91 ends along the long axis 65 and may be actuated in a number of different ways, such as by a motor 81. The motor 81 may be a stepper motor operating in discrete steps to precisely control reciprocation of shaft 80. Although the motor 81 is shown in FIG. 10 within the proximal end 90 of handle 43, it could be remotely located in the control box 50 or placed outside of the handle 43 while still controlling operation of the reciprocating shaft 80 to control operation of the external electrode sheath 61 and the positioning member 43.

FIGS. 10-14 illustrate exemplary operating components within handle 43 as viewed from the bottom of the handle 43. With continuing reference to FIGS. 10-14, the handle 43 comprises a chassis 82 cradled or nested within the handle 43. The chassis 82 may be manufactured as a single component or formed from an assembly of multiple components. The chassis 82 is coupled to and/or mounted within the handle 43 to provide a support structure for the other operating components within the handle 43. The chassis 82, including both proximal and distal stops (not labeled) for the electrode sheath 61 (which form part of the chassis) is manufactured in a manner allowing for minimal tolerances between operating components, which in turn allows for the ability to finely control movements (often much less than a millimeter) of the components therein. Chassis 82 includes a raised island portion, shown as 82a in FIGS. 10-14, along the long axis 65. As shown in FIG. 10, the raised island portion 82a of the chassis may have tapered sides that are designed to mate with an engaging member 86, as will be described in further detail below.

The chassis 82 further houses an external electrode sheath carrier 83. The external electrode sheath carrier 83 is seated longitudinally within the chassis and defines a long axis 65 over which it is centered. As shown in FIG. 10, the external electrode sheath carrier 83 is an approximately rectangular piece operably mated at its proximal end to the reciprocating shaft 80. The distal end of the external electrode sheath carrier 83 is coupled to the external electrode sheath 61, which extends from the distal end of the handle 43. The external electrode sheath carrier 83 is adapted to move proximally and distally relative to the chassis 82 and handle 43. In one embodiment, the movements of the external electrode sheath carrier 83 and reciprocating shaft 80 are proportional. Because the external electrode sheath 61, external electrode sheath carrier 83, and reciprocating shaft 80 are all coupled together they will effectively move together. Said another way, when the reciprocating shaft 80 slides distally it forces the external electrode sheath carrier 83 to slide distally, which forces the external electrode sheath 61 to slide distally.

The handle 43 as shown in FIGS. 10-14 also houses an internal sheath 62 mounted to the chassis and disposed within the lumen 64 of the external electrode sheath 61 along its long axis 65. The internal sheath 62 is sized to fit within the lumen of the external electrode sheath 61 and is best shown in FIG. 10 extending from the proximal end of the external electrode sheath 61. The internal sheath 62 is rigidly mounted to the raised island portion 82a of the chassis 82 and thus, remains stationary through the porous implant deployment and reload operations.

Handle 43 also comprises the positioning member 63 and a positioning member carrier 84, as shown in FIGS. 10-14. The positioning member 63 is coupled to the push rod carrier 84 at the distal end of the positioning member carrier 84 and is disposed within the lumen 73 of the internal sheath 62 along long axis 65. Positioning member 63 is sized to slideably fit within the lumen 73 of the internal sheath 62 so that it can slide distally to push one or more porous implants 66-67 toward the distal tip 60 of the catheter 41. The positioning member carrier 84 is disposed within the external electrode sheath carrier 83 and is slideably positioned along the long axis 65 of the external electrode sheath carrier 83. Because the positioning member carrier 84 is operably mated to the positioning member 63, movement of the positioning member carrier 84 proportionally effectuates movement of the positioning member 63, as will be described in further detail below.

With continuing reference to FIGS. 10-14, the handle 43 further comprises first 85 and second 86 engaging members. In one embodiment, first 85 and second 86 engaging members may be biasing members, such as leaf-type springs, for example. First engaging member 85 is coupled to the external electrode sheath carrier 83 at its proximal end and defines at least one arm 87 adapted to releaseably engage the positioning member carrier 84. Engagement of the positioning member carrier 84 by the at least one arm 87 of the first engaging member 85 enables and/or prevents movement of the positioning member carrier 84 relative to the external electrode sheath carrier 83. The second engaging member 86 is coupled to the positioning member carrier 84 and also defines at least one arm 88 adapted to releaseably engage the raised island portion 82a of the chassis 82. Engagement of the raised island portion 82a of the chassis 82 by the at least one arm 88 of the second engaging member 86 enables and/or prevents movement of the positioning member carrier 84 relative to the external electrode sheath carrier 83.

In operation, when the reciprocating shaft 80 drives the external electrode sheath carrier 83 (which in turn drives both the external electrode sheath 61 and first engaging member 85) proximally 90, it deploys a porous implant 66 by forcing a first porous implant 66 toward the distal end 60 and out of the slit opening 72 (best shown in FIGS. 7-8). When the reciprocating shaft 80 drives the external electrode sheath carrier 83 (which in turn drives both the external electrode sheath 61 and first engaging member 85) distally 91, it reshrouds the internal sheath 62 and reloads another porous implant 67 into the external electrode sheath 61 and positions the external electrode sheath 61 in a ready-to-deploy position (best shown in FIGS. 8-9). Movement of the external electrode sheath carrier 83 by the reciprocating shaft 80 also selectively actuates the positioning member carrier 84 via engagement with one or both of the engaging members 85 and 86 to reload another porous implant and get the components in a ready-to-deploy position, as will be described in further detail below.

FIG. 10 illustrates an initial stage or state of the components within handle 43 before a first porous implant is deployed. As shown in FIG. 10, the reciprocating shaft 80 is fully extended (out of the motor 81) toward the distal end 91 of the handle 43 in this initial state position before any deployments have occurred. FIG. 10 further illustrates the reciprocating shaft 80, external electrode sheath carrier 83, and external electrode sheath 61 at their most distal positions before any deployment has occurred.

Figure 11:
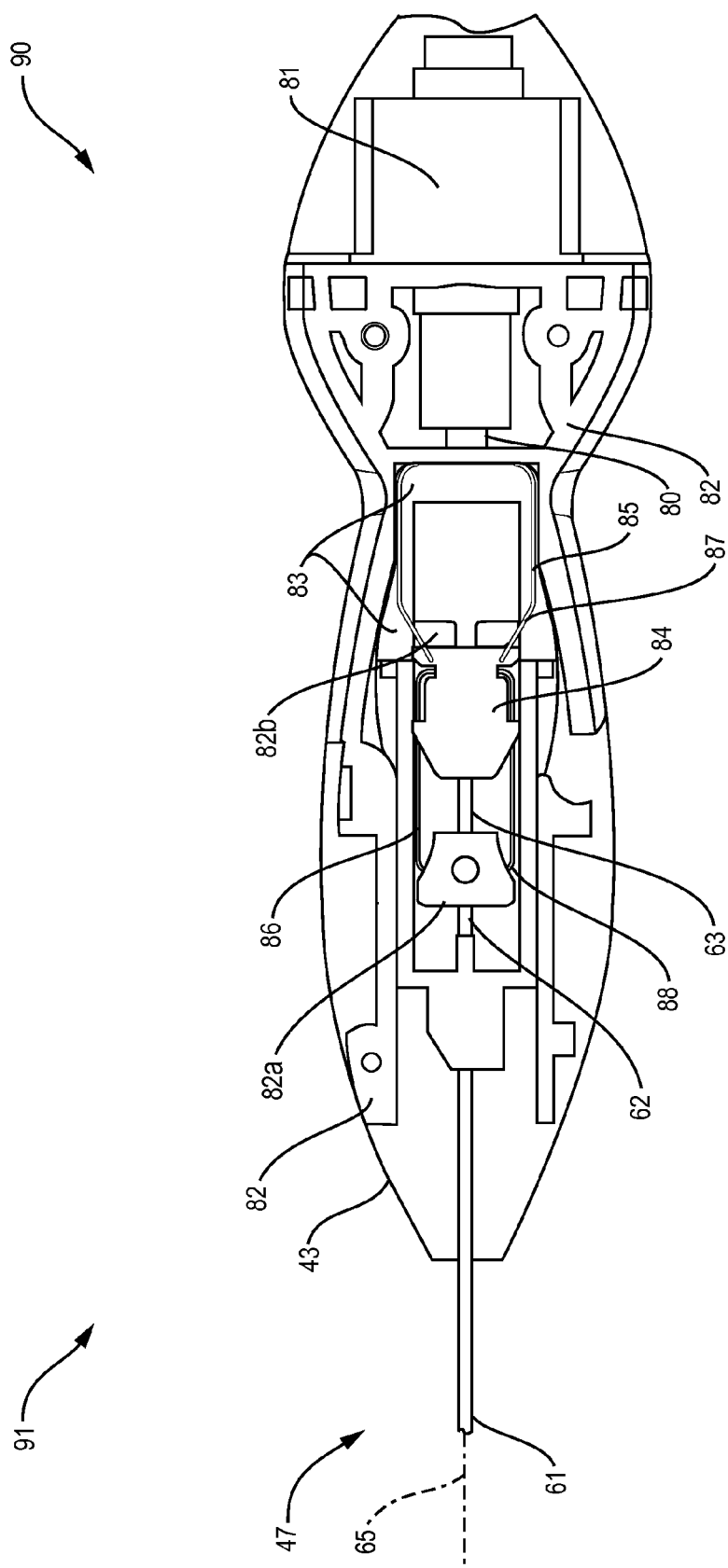
FIG. 11 is a cross-sectional bottom view of the handle of a sterilization device after the first porous implant has been deployed.

FIG. 11 illustrates a bottom view of the handle 43 after deployment of the first porous implant and after the reciprocating shaft 80, external electrode sheath carrier 83, external electrode sheath 61, and first engaging member 85 have all slid toward the proximal end 90 of handle 43. When the reciprocating shaft 80 slides proximally (or retracts into motor 81) it also slides both the external electrode sheath carrier 83 and external electrode sheath 61 proximally while the positioning member 63 remains stationary. The proximal movement of the external electrode sheath 61 (against a stationary positioning member 63) forces the first porous 66 implant toward the distal tip 60 of the catheter 47 and out of the slit opening 72 (best shown in FIG. 7) to dispose the first porous implant 66 within a first fallopian tube. Movement of the external electrode sheath carrier 83 is stopped (in the proximal direction 90) by the chassis 82 at the appropriate predetermined position. During the deployment operation, the internal sheath 62, positioning member 63 and positioning member carrier 84 all remain stationary. While the external electrode sheath carrier 83 moves proximally, the positioning member carrier 84 is prevented from sliding proximally by the presence of another raised island portion 82b of the chassis, which acts as a hard-stop, as shown in FIG. 11.

After the first porous implant is deployed, the internal sheath must be reshrouded and a second porous implant must be reloaded into the external electrode sheath 61. Reshrouding and reloading generally occurs in two stages, illustrated in two parts in FIGS. 11 and 12.

Figure 12:
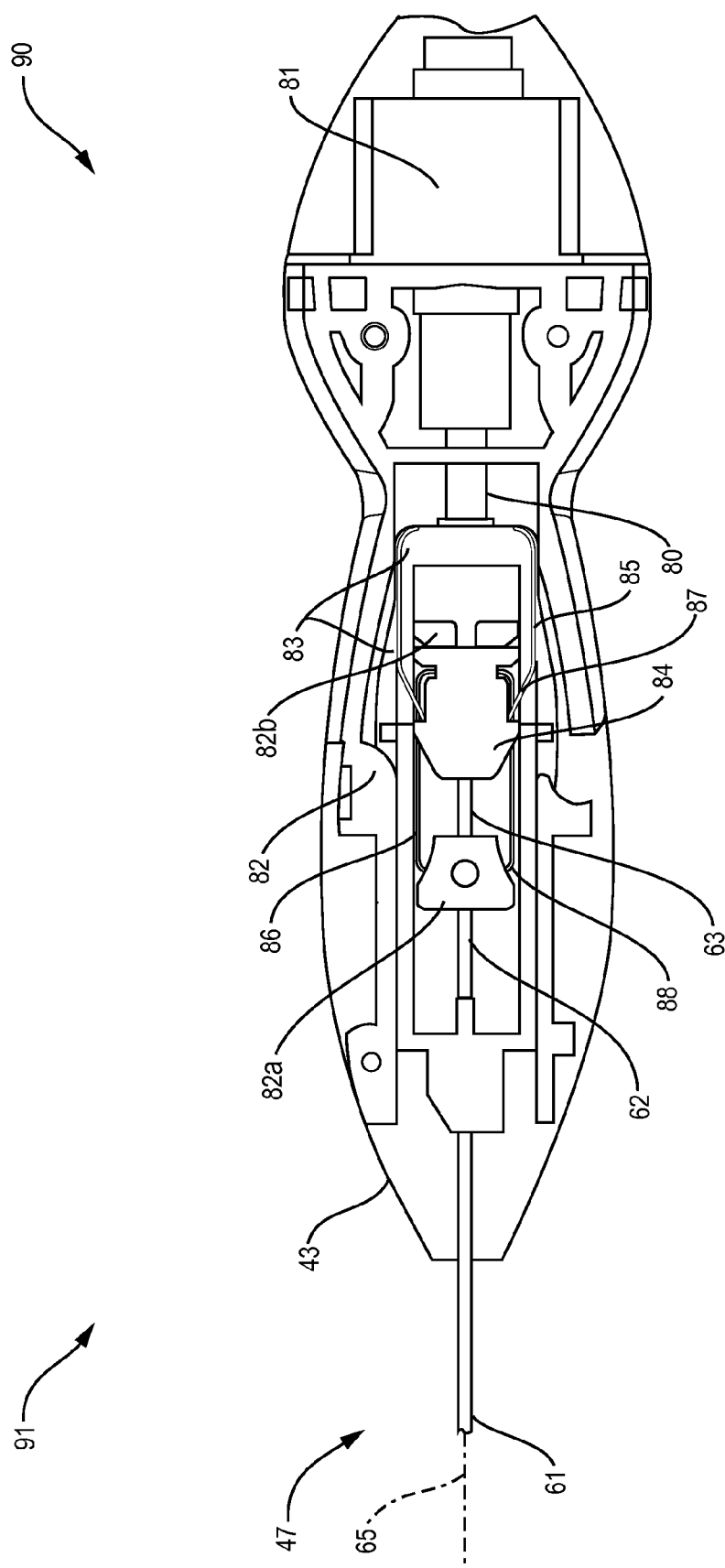
FIG. 12 is a cross-sectional bottom view of the handle of a sterilization device during reload (part 1) of a second porous implant.

As shown in FIG. 12, the reciprocating shaft 80 begins to move toward the distal end 91 of the handle 43. Distal movement of the reciprocating shaft 80 forces the external electrode sheath carrier 84 and attached first engaging member 85 (as well as the external electrode sheath 61) to move toward distal end 91 of the handle 43. This distal movement of the distal most end of the external electrode sheath 61 of the catheter 47 reshrouds the internal sheath to help get the device closer to its second ready-to-deploy position.

With continued reference to FIG. 12 and the first stage of the reload operation, as the first engaging member 85 moves distally the at least one arm 87 contacts the positioning member carrier 84. The first engaging member 85 may be a biasing member, such as a leaf-type spring, and may comprise two arms 87, which move out and around the positioning member carrier 84 and then snap into position on the positioning member carrier 84 at a predetermined location. The first engagement member 85 may be configured to provide no resistance when sliding proximally, but will provide resistance in the distal direction once it has snapped into place around the positioning member carrier 84, thus having the ability to push the positioning member carrier distally. At this stage, the first engaging member 85 and positioning member carrier 84 are now coupled together and will move together distally as one. However, it is important to note that in some designs the dimensional tolerances may be so small that a small gap or delay may occur between movement of the first engaging member 85 and movement of the positioning member carrier 84. This small gap or space may be intentionally designed and intended to allow the first engagement member 85 to move a millimeter or even a few millimeters before effectuating movement of the positioning member carrier 84.

Figure 13:
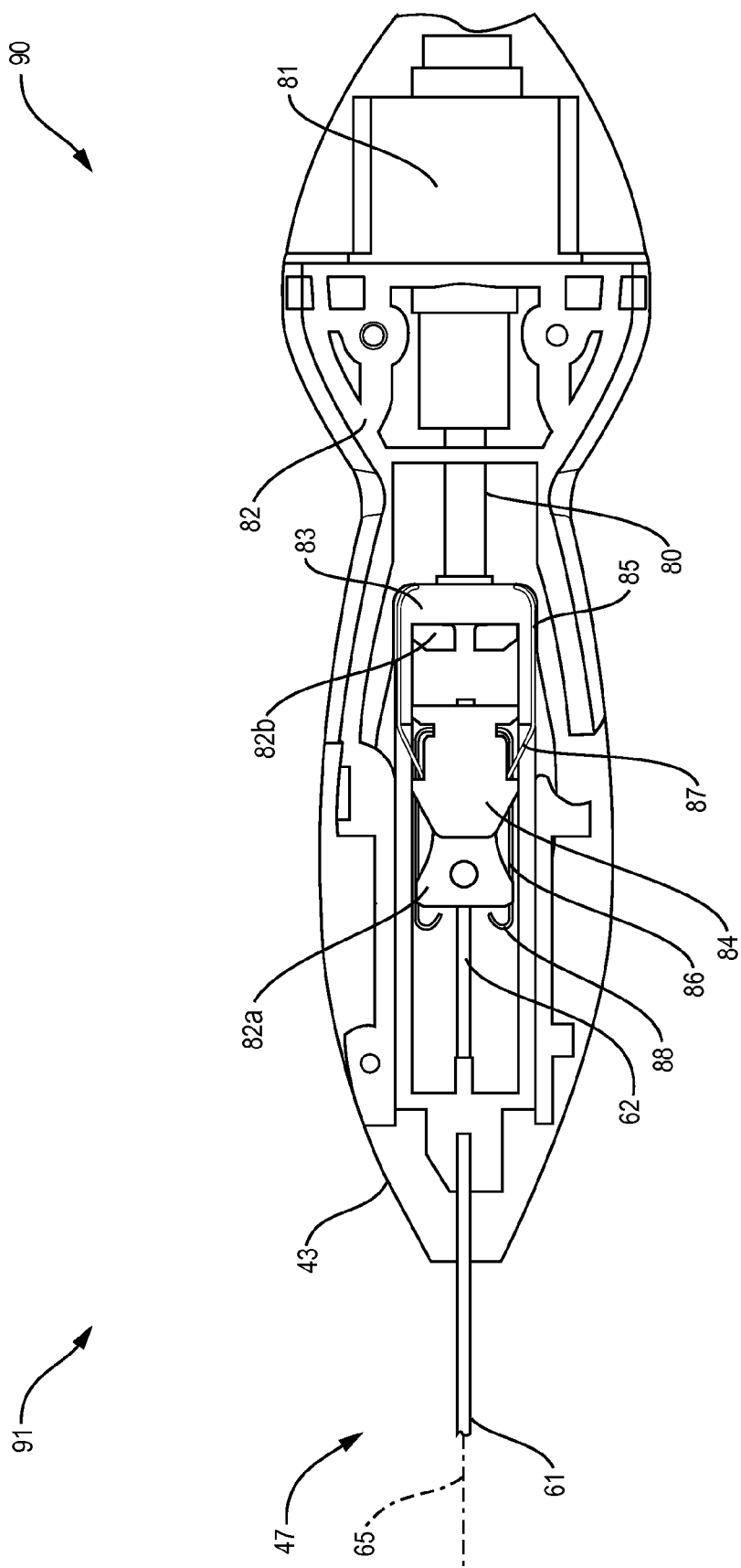
FIG. 13 is a cross-sectional bottom view of the handle of a sterilization device during reload (part 2) of a second porous implant.

The second stage of the reload operation, shown in FIG. 13, continues with reciprocating shaft 80 continuing to slide toward the distal end 91, which now also forces the positioning member carrier 84 (and the second engagement member 86 mounted thereon) distally via the engagement between the first engagement member 85 (mounted to the external electrode sheath carrier 83) and the positioning member carrier 84. As shown in FIG. 13, the positioning member carrier 84 slides toward the distal end 91 until it contacts the raised island portion 82a of the chassis, which acts as a hard-stop to prevent any further distal movement of the positioning member carrier 84. As the positioning member carrier 84 is moving distally, the second engaging member 86 (mounted thereon) is also moving distally and at least one of the arms 88 of the second engaging member 86 contacts the raised island portion 82a of the chassis 82. In one embodiment, the second engaging member 86 may be a biasing member, such as a leaf-type spring, having two arms 88, which ride out around and then snap into place around the raised island portion 82a of the chassis 82. The second engaging member 86 may be configured to provide no resistance when moving distally but will provide resistance in the proximal direction once it has snapped into place around the raised island portion 82a of the chassis 82, to prevent the positioning member carrier 84 from moving proximally. Once the second engagement member 86 and raised island portion 82a of the chassis are coupled together (as shown in FIG. 13) the positioning member carrier 84 cannot move. The above described distal movement of the positioning member carrier 84 (which in turn moved the positioning member 63 distally) forces a second porous implant out of the internal sheath and into the distal tip of the external electrode sheath 61 in a second ready-to-deploy position.

Figure 14:
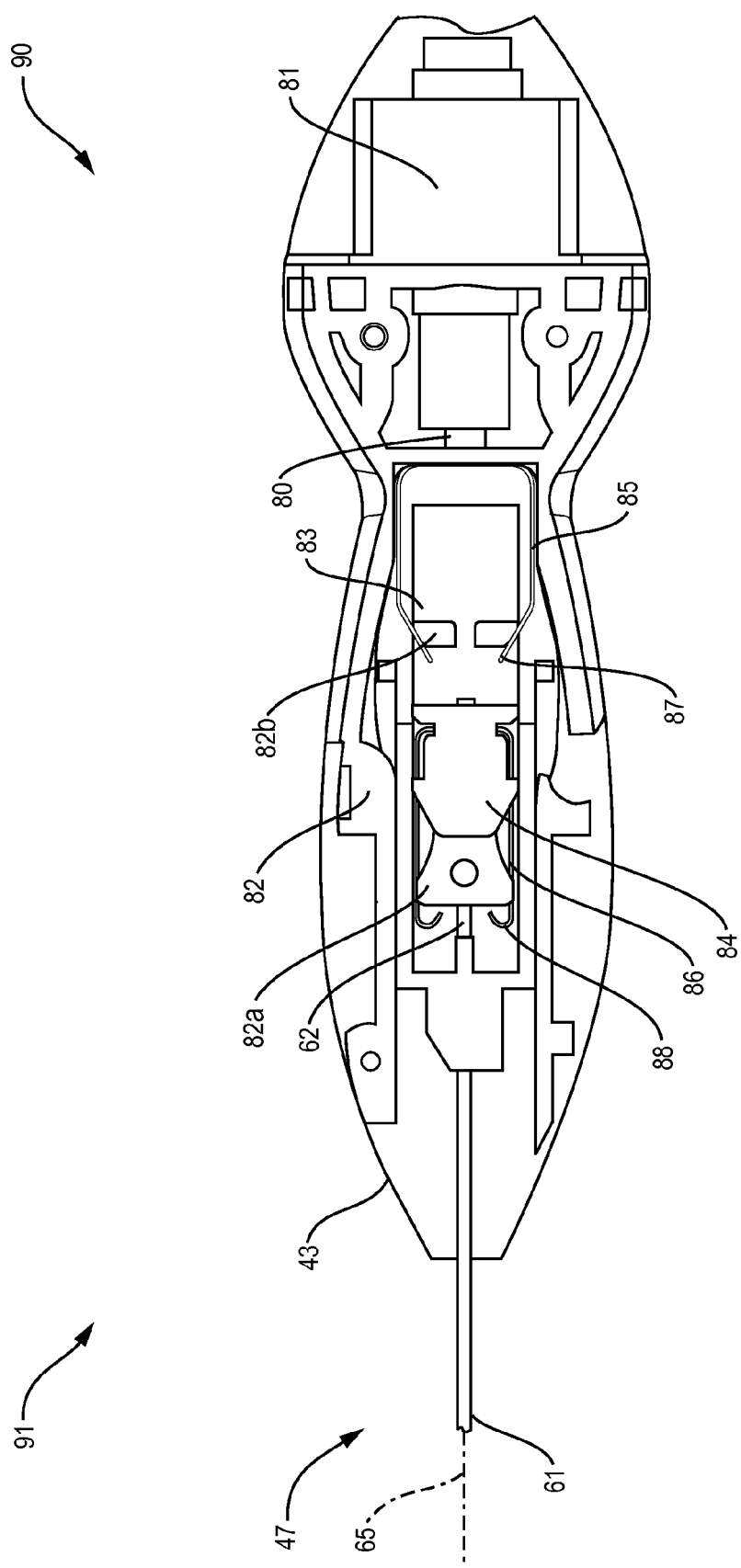
FIG. 14 is a cross-sectional bottom view of the handle of a sterilization device after the second porous implant has been deployed.

The final stage of the operation involves the deployment of the second porous implant, as shown in FIG. 14. The deployment of the second porous implant is quite similar to the deployment of the first porous implant in that the reciprocating shaft 80, external electrode sheath carrier 83 and external electrode sheath 61 all move proximally (while the positioning member 63 and positioning member carrier 84 remain stationary) to force the second implant into the distal tip 60 of the catheter 47 and out of the slit opening 72 (best shown in FIG. 9) into a fallopian tube. However, as can be seen in FIG. 14, the positioning member carrier 84 is in a different position in comparison to its position during the deployment of the first implant 66 by virtue of the reload procedures (shown and described with reference to FIGS. 12 and 13).

Figure 15:
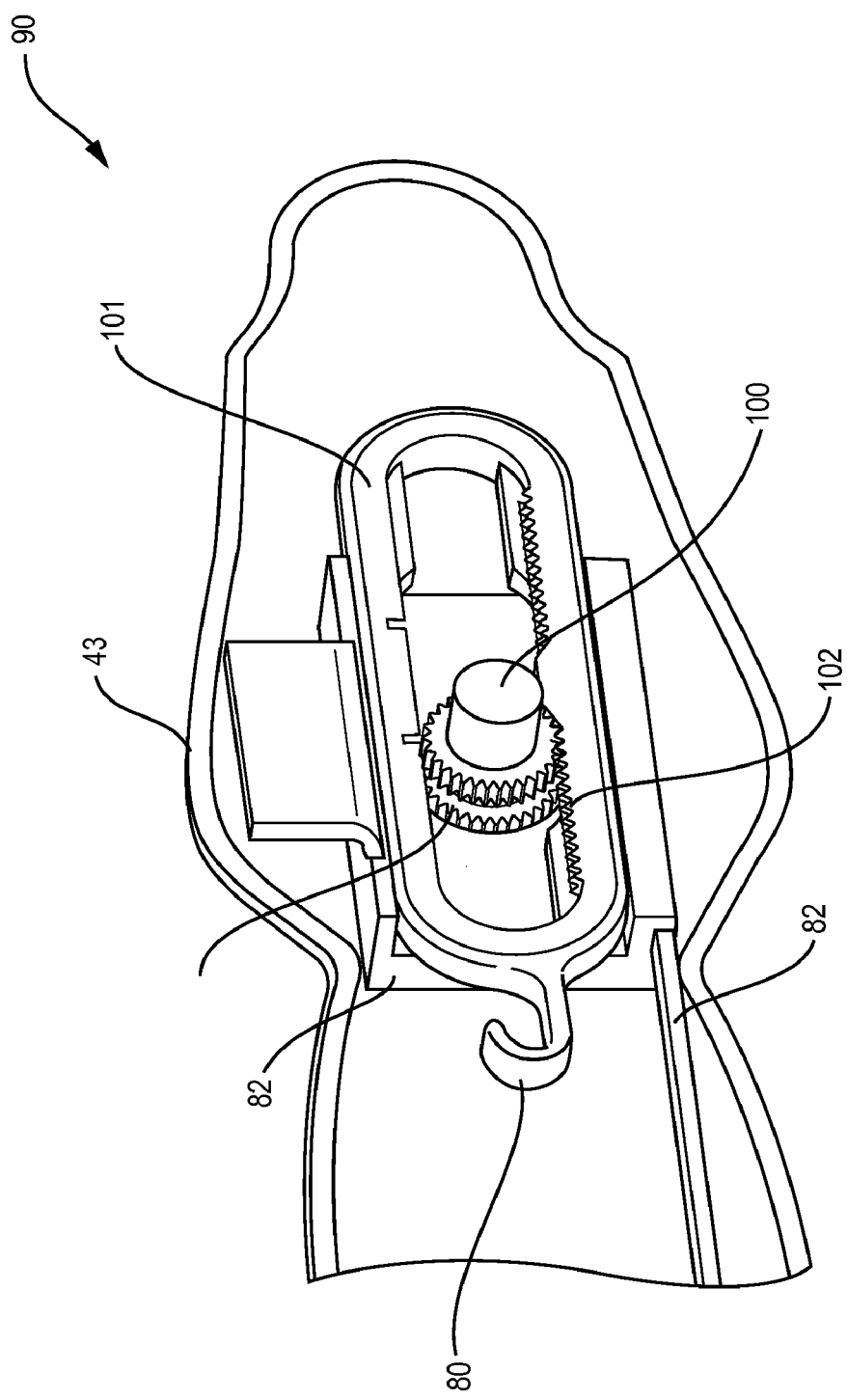
FIG. 15 is a partial perspective view of a rack and pinion mechanism in the handle of the sterilization device.
Figure 16:
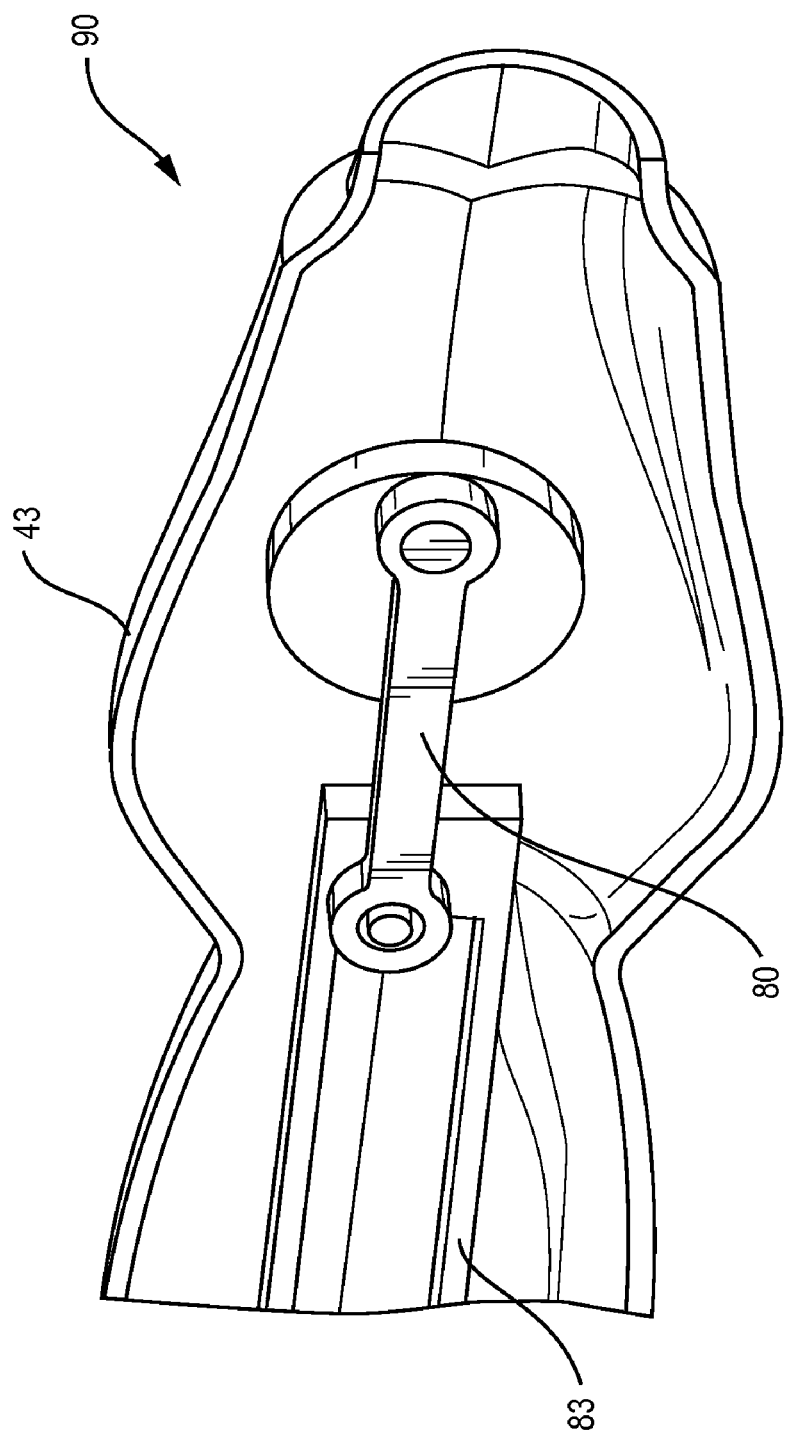
FIG. 16 is a partial perspective view of a rotating four bar mechanical linkage in the handle of the sterilization device.

In the embodiments shown and described above with reference to FIGS. 10-14, the reciprocating shaft 80 is moved via a motor 81 residing at the proximal end 90 of the handle 43. However, in alternative embodiments, a mechanical mechanism may be used in place of the motor 81 to reciprocate the shaft 80. In one embodiment, a rack and pinion mechanism may be used to reciprocate the shaft 80, as shown in FIG. 15. In another embodiment, a rotating four-bar linkage may be used to reciprocate the shaft 80, as shown in FIG. 16. In both of these embodiments, the primary difference lies in the mechanism used to drive the reciprocating motion of the shaft 80; the operations and design of the external electrode sheath carrier 83, the external electrode sheath 61, the internal sheath 62, the positioning member 63, the positioning member carrier 84, the chassis 82, and the first 85 and second 86 engaging mechanisms would all remain the same as described above.

With reference now to FIG. 15, a rack and pinion mechanism is disposed within handle 43 toward its proximal end 90. The rack and pinion mechanism functionally takes the place of the reciprocating shaft 80 and electrode sheath carrier 83 (described above). This system uses a pinion gear 100 to turn and create linear displacement of an elongated rack 101, which in turn drives the external electrode sheath 61 and/or the internal sheath 62 (if provided) and/or the positioning member 63, as described above. The rack 101 is specifically designed with two or more sets of internal teeth 102 on opposite sides of an opening. The teeth 102 of rack 101 are designed to mate with teeth 103 on round pinion gear 100. Upon reaching one end of one set of teeth 102 on the rack 101, the pinion gear 100 can then be translated along its axis so that it engages the second set of teeth 102 and disengages the first set of teeth 102. When the rack 101 then continues to translate in the original direction, the pinion gear 100 then rotates in the opposite direction. The rack 101 may be driven by a single tension or compression spring, or other type of biasing member that. The rack and pinion mechanism converts force in a single direction into motion in two or more directions, which is necessary to effectuate the reload operations of the catheter 47 and handle 43 described above. By having the pinion gear 100 change directions, the components within the handle 43 described above can be moved in multiple directions, thereby executing the reload function.

With reference now to FIG. 16, a rotating four-bar linkage 110 is disposed within handle 43 at its proximal end 90 in place of a motor to reciprocate the shaft 80. By rotating one link of the four-bar linkage 110, the reciprocating shaft 80 can be actuated, thus effecting movement of the external electrode sheath carrier 83, etc. The four-bar linkage 110 could be driven using a spring-loaded rack, a torsion or clock spring, or an electric stepper motor. This four-bar linkage 110 can provide a purely mechanical means for reciprocating the shaft 80 and can thus actuate the external electrode sheath carrier 83 to deploy and reload porous implants, as described above.

We have described various devices and methods in the context of placing a catheter into the fallopian tubes, wounding tissue at target locations and deploying implants into each fallopian tubes at said target locations. However, these devices and methods may also be used in various other lumens, vessels and/or body locations. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A device configured for insertion into a fallopian tube, comprising:
   a distal end and a proximal end having a handle thereon;
   an external electrode sheath having a lumen sized for housing a first porous implant at the distal end and along a long axis thereof, the external electrode sheath configured to slide distally and proximally along its long axis relative to the handle and including at least one ring electrode disposed about its outer diameter for wounding an epithelial layer of a fallopian tube;
   an internal sheath longitudinally disposed within the lumen of the external electrode sheath at its distal end and having a lumen sized for housing a second porous implant along the long axis thereof; and
   a positioning member slideably disposed within the lumen of the internal sheath proximal to the first and second porous implants along the long axis, the positioning member configured to slide relative to the handle and toward the distal end of the catheter;
   wherein sliding at least one of the external electrode sheath or the positioning member relative to one another disposes the first porous implant within a first fallopian tube and disposes the second porous implant within a second fallopian tube.

2. The device of claim 1, wherein the first and second implants at least one of (i) have pore sizes averaging approximately 40 to 200 microns and (ii) have an overall length between approximately 3 mm and approximately 5 mm.

3. The device of claim 1, wherein the first porous implant at least one of (i) is slid toward the distal end, at least partially, by the second porous implant sliding toward the distal end; and (ii) is slid toward the distal end, at least partially, by the positioning member sliding toward the distal end.

4. The catheter of claim 1, wherein sliding the external electrode sheath toward the proximal end disposes the first porous implant within the first fallopian tube at a position where wounding via the at least one ring electrode occurred.

5. The device of claim 4, wherein simultaneously sliding the external electrode sheath and the positioning member toward the distal end of the catheter reshrouds the internal sheath and positions the second porous implant within the distal end of the external electrode sheath ready for deployment into a second fallopian tube at a position where wounding via the ring electrodes occurred.

6. The device of claim 1, further comprising at least one of (i) at least one pad electrode disposed about the outer surface of the external electrode sheath and (ii) at least one optical member disposed about the outer surface of the external electrode sheath.

7. The device of claim 1, wherein at least one of the first and second porous implants comprises an inner layer and an outer layer surrounding the inner layer.

8. The device of claim 7, wherein the outer layer is comprised, by volume, of approximately 100% Silicon, and the inner layer is comprised, by volume, of approximately 85% Silicon and approximately 15% Tantalum.

9. A catheter device configured for insertion into a fallopian tube, comprising:
   a distal end and a proximal end having a handle thereon;
   an external electrode sheath having a lumen sized for housing two porous implants at the distal end and along a long axis thereof and configured to slide distally and proximally along its long axis relative to the handle; and
   a positioning member disposed within the lumen of the external electrode sheath proximal to the two porous implants along the long axis, the positioning member configured to slide relative to the handle;
   wherein sliding the external electrode sheath toward the proximal end of the catheter disposes at least one of the two porous implants within a fallopian tube.

10. The catheter of claim 9, wherein the external electrode sheath further comprises ring electrodes disposed about its outer diameter for wounding an epithelial layer of a first fallopian tube, wherein a first porous implant is disposed within a first fallopian tube at the position where wounding of the epithelial layer of the first fallopian tube via the ring electrodes occurred.

11. The catheter of claim 9, wherein the handle further comprises:
   a chassis cradled within the handle;
   an external electrode sheath carrier seated within the chassis and defining a long axis, wherein a distal end of the external electrode sheath carrier is coupled to the external electrode sheath, wherein the external electrode sheath extends from the distal end of the handle;
   a reciprocating shaft coupled to the external electrode sheath carrier at its proximal end and adapted to move the external electrode sheath carrier proximally and distally relative to the handle;
   an internal sheath mounted to the chassis and disposed within a lumen of the external electrode sheath;
   a positioning member carrier disposed within the external electrode sheath carrier and slideable along the long axis of the external electrode sheath carrier, wherein the positioning member carrier is coupled to the positioning member, and wherein the positioning member is disposed within a lumen of the internal sheath;
   a first engaging member coupled to the external electrode sheath carrier and defining at least one arm adapted to releaseably engage the positioning member carrier to enable or prevent movement of the positioning member carrier relative to the external electrode sheath carrier; and
   a second engaging member coupled to the push rod carrier and defining at least one arm adapted to releaseably engage the chassis to enable or prevent movement of the positioning member carrier relative to the external electrode sheath carrier;
   wherein the reciprocating shaft drives the external electrode sheath carrier proximally and distally relative to the chassis to deploy the implants and selectively actuate the positioning member carrier via engagement with one or both of the engaging members.

12. The catheter of claim 9, wherein the external electrode is configured to slide within a range of about 5 mm and 25 mm.

13. The catheter of claim 9, wherein the positioning member is positioning member is configured to slide within a range of about 2 mm to 10 mm.

14. A method for occluding two fallopian tubes using a single catheter containing two porous implants, comprising:
   inserting a catheter into a first fallopian tube, wherein the catheter comprises:
      a distal end and a proximal end having a handle thereon;
      an external electrode sheath having a lumen sized for housing two porous implants at the distal end and along a long axis thereof, the external electrode sheath having ring electrodes disposed about its outer diameter for wounding an epithelial layer of a fallopian tube; and a positioning member disposed within the lumen of the external electrode sheath proximal to the two porous implants along the long axis, the positioning member configured to slide relative to the handle;

wounding an epithelial layer of a first fallopian tube using the ring electrodes on the external electrode sheath;

sliding the external electrode sheath toward the proximal end of the catheter to dispose a first porous implant within a first fallopian tube where wounding occurred;

removing the catheter from the first fallopian tube and inserting the catheter into a second fallopian tube;

wounding an epithelial layer of a second fallopian tube using the ring electrodes on the external electrode sheath; and sliding the external electrode sheath toward the proximal end of the catheter to dispose a second porous implant within a second fallopian tube where wounding occurred.

15. The method of claim 14, wherein the catheter further comprises an internal sheath longitudinally disposed within the lumen of the external electrode sheath and having a lumen sized for housing the second porous implant along the long axis thereof;

wherein simultaneously sliding the external electrode sheath and the positioning member toward the distal end of the catheter reshrouds the internal sheath after deployment of the first porous implant to position the second porous implant at the distal end of the catheter within the external electrode sheath.

16. The method of claim 15, wherein sliding the positioning member pushes at least one of the two porous implants out of the internal sheath.

17. The method of claim 14, further comprising sliding the positioning member pushes at least one of the two porous implants toward the distal end of the catheter.

18. The method of claim 14, further comprising sliding the external electrode sheath toward the proximal end of the catheter to dispose the second porous implant within the second fallopian tube while the positioning member is stationary.

19. The method of claim 14, further comprising sliding the positioning member distally to position the second porous implant for deployment within the second fallopian tube.

* * * * *